(12) United States Patent
Stemmer

(10) Patent No.: US 9,476,955 B2
(45) Date of Patent: Oct. 25, 2016

(54) METHOD AND CONTROL DEVICE TO OPERATE A MAGNETIC RESONANCE SYSTEM

(71) Applicant: Alto Stemmer, Erlangen (DE)

(72) Inventor: Alto Stemmer, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 880 days.

(21) Appl. No.: 13/847,656

(22) Filed: Mar. 20, 2013

(65) Prior Publication Data
US 2013/0249548 A1 Sep. 26, 2013

(30) Foreign Application Priority Data
Mar. 20, 2012 (DE) .......... 10 2012 204 434

(51) Int. Cl.
| | |
|---|---|
| G01R 33/54 | (2006.01) |
| G01R 33/483 | (2006.01) |
| G01R 33/44 | (2006.01) |
| A61B 5/055 | (2006.01) |
| G01R 33/48 | (2006.01) |

(52) U.S. Cl.
CPC ............ *G01R 33/543* (2013.01); *G01R 33/44* (2013.01); *G01R 33/4835* (2013.01); *A61B 5/055* (2013.01); *G01R 33/4824* (2013.01)

(58) Field of Classification Search
CPC G01R 33/44; G01R 33/543; G01R 33/4824; G01R 33/4835; A61B 5/055
See application file for complete search history.

(56) References Cited

U.S. PATENT DOCUMENTS

| | | | |
|---|---|---|---|
| 6,771,069 B2 | 8/2004 | Asano et al. | |
| 6,853,188 B2 | 2/2005 | Feinberg et al. | |
| 7,840,049 B2 | 11/2010 | Stemmer | |
| 8,723,516 B2* | 5/2014 | Wheaton | G01R 33/5607 324/307 |
| 2003/0011367 A1 | 1/2003 | Asano et al. | |
| 2003/0169042 A1 | 9/2003 | Feinberg et al. | |
| 2004/0263166 A1 | 12/2004 | Kluge | |
| 2005/0017719 A1 | 1/2005 | Heubes | |
| 2007/0249929 A1 | 10/2007 | Jeong et al. | |
| 2010/0259260 A1 | 10/2010 | Lee et al. | |
| 2011/0210733 A1* | 9/2011 | Wheaton | G01R 33/5607 324/309 |
| 2011/0275926 A1 | 11/2011 | Du | |
| 2014/0028314 A1* | 1/2014 | Paul | G01R 33/387 324/309 |

(Continued)

OTHER PUBLICATIONS

Guenther et al. "Simultaneous Spin-Echo Refocusing," Magnetic Resonance in Medicine, vol. 54, (2005) pp. 513-523.

(Continued)

*Primary Examiner* — Dixomara Vargas
(74) *Attorney, Agent, or Firm* — Schiff Hardin LLP

(57) ABSTRACT

In a method and a control device for operation of a magnetic resonance tomography system to generate image data, multiple of slices in an examination subject are initially excited at a first time interval by a respective RF slice excitation pulse of a series of spatially selective slice excitation pulses. An RF refocusing pulse is then emitted at a second time interval after the first excitation pulse or after the last excitation pulse of the series of RF slice excitation pulses. At least one additional RF refocusing pulse is emitted at a third time interval after a preceding RF refocusing pulse. The third time interval is twice as long as the second time interval. The width of the RF refocusing pulses is selected to generate a number of chronologically separate echo signals per RF refocusing pulse for simultaneous refocusing of all excited slices.

16 Claims, 11 Drawing Sheets

(56) References Cited

U.S. PATENT DOCUMENTS

2014/0210471 A1* 7/2014 Stemmer .......... G01R 33/56554
 324/309
2015/0042336 A1* 2/2015 Feiweier ............ G01R 33/4833
 324/309

OTHER PUBLICATIONS

Schick, Splice:Sub-Second Diffusion-Sensitive MR Imaging Using a Modified Fast Spin-Echo Acquisition Mode, Magnetic Resonance in Medicine, vol. 38, Issue 4, (1997) pp. 636-644.

Pipe, "Motion Correction with Propeller MRI: Applicantion to Head Motion and Free-Breathing Cardiac Imaging," Magnetic Resonance in Medicine, vol. 42 (1999) pp. 963-969.
Oshio et al. GRASE (Gradient-and Spin Echo) Imaging: A Novel Fast MRI Technique, Magnetic Resonance in Medicine, vol. 20 (1991) pp. 344-349.
Lee et al., Multiplex RARE: A Simultaneous Multislice Spin-Echo Sequence That Fulfils CPMG Conditions, Magnetic Resonance in Medicine, vol. 64, (2010) pp. 299-305.
Scheenen et al., MRI of the Human Prostate in Vivo at 7T, Proc. Intl. Soc. Mag. Reson. Med 19 (2011) p. 592.
Pipe et al.; "Multishot Diffusion-Weighted FSE using Propeller MRI" Magnetic Resonance in Medicine vol. 47:pp. 42-52 (2002).

* cited by examiner

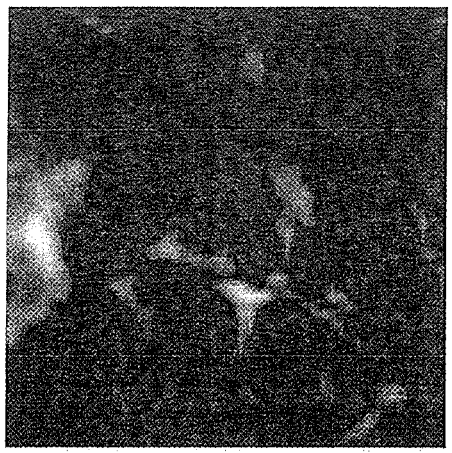
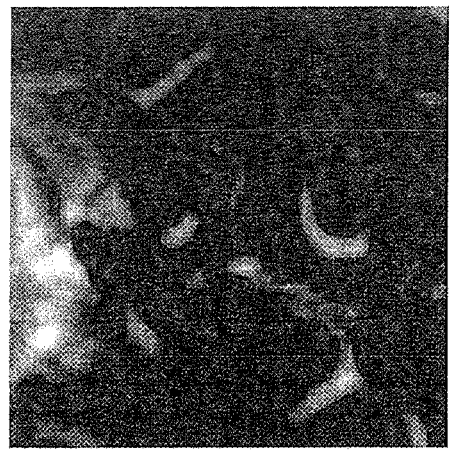
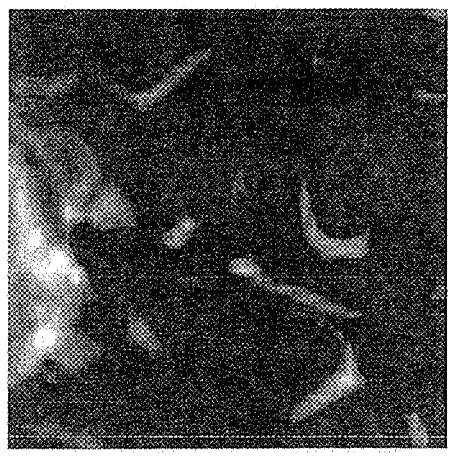
FIG 11
$S_1$
$S_2$

METHOD AND CONTROL DEVICE TO OPERATE A MAGNETIC RESONANCE SYSTEM

BACKGROUND OF THE INVENTION

1. Field of the Invention

The invention concerns a method to operate a magnetic resonance tomography system (MT system) to generate magnetic resonance image data of an examination subject, of the type wherein a number of slices in the examination subject are excited within a sequence module by respective RF slice excitation pulses of a series of a spatially selective RF slice excitation pulses, and then multiple RF refocusing pulses are emitted, and wherein the width of the RF refocusing pulses for generation of a number of time-separated echo signals is selected per RF refocusing pulse such that it encompasses at least a portion of an excitation volume of all excited slices for simultaneous refocusing of all excited slices. Furthermore, the invention concerns a method to generate magnetic resonance image data of an examination subject, wherein raw data are used that were acquired by a magnetic resonance tomography system using such a method. Moreover, the invention concerns a control device for a magnetic resonance tomography system to implement such a method, as well as a magnetic resonance tomography system with such a control device.

2. Description of the Prior Art

In a magnetic resonance system, the body to be examined is typically exposed to a relatively strong basic magnetic field (for example 1.5 Tesla, 3 Tesla or 7 Tesla) produced by a basic magnetic field system. After application of the basic field, nuclei in the examination subject with a non-vanishing nuclear magnetic dipole moment (frequently also called spin) align along the field. This collective response of the spin system is described with the macroscopic "magnetization". The macroscopic magnetization is the vector sum of all microscopic magnetic moments in the subject at a specific location. In addition to the basic field, a magnetic field gradient with which the magnetic resonance frequency (Larmor frequency) is determined at the respective location is additionally applied by a gradient system. From a radio-frequency transmission system, radio-frequency excitation signals (RF pulses) are then emitted by suitable antenna devices, which lead to the nuclear spins of specific nuclei being excited to resonance (i.e. at the Larmor frequency present at the respective location) by this radio-frequency field by being flipped by a defined flip angle relative to the magnetic field lines of the basic magnetic field. If such an RF pulse acts on spins that are already excited, these can be flipped into another angle position or even be flipped back into an initial state parallel to the basic magnetic field. During the relaxation time of the excited nuclear spins, radio-frequency signals (known as magnetic resonance signals) are radiated upon resonance, and these magnetic resonance signals are received by suitable reception antennas, and then are processed further. The acquisition of the magnetic resonance signals takes place in the spatial frequency domain (known as "k-space"). K-space is traversed (i.e., the acquired data are entered therein at points) over time along a "gradient trajectory" (also called a "k-space trajectory") defined by the switching of the gradient pulses during a measurement of a slice, for example. Moreover, the RF pulses must be emitted in coordination, matching in time. Finally, the desired image data can be reconstructed by means of a two-dimensional Fourier transformation from the "raw data" acquired in such a manner.

Defined, predetermined pulse sequences (i.e. sequences of defined RF pulses and gradient pulses in different directions and of readout windows during which the reception antennas are switched to receive and the magnetic resonance signals are received and processed) are typically used to control a magnetic resonance tomography system in the measurement. In a measurement protocol, these sequences are parameterized in advance for a desired examination, for example a defined contrast of the calculated images. The measurement protocol can also include additional control data for the measurement. There are a number of magnetic resonance sequence techniques according to which pulse sequences can be designed. One of the major challenges in the future development in magnetic resonance imaging is an acceleration of magnetic resonance sequence techniques without wide-ranging compromises with regard to resolution, contrast and tendency towards artifacts. An increase of the examination speed leads to a smaller exposure time of the patient, who must remain at rest within the (most often quite narrow) magnetic resonance tomography scanner over a longer period of time. Because the applications and possibilities of magnetic resonance imaging are diversifying and thus the number of measurement protocols available to be executed per examination grows, a reduction of the measurement time for individual measurement protocols becomes all the more important. In addition, the examination duration of an MR examination is directly linked with the patient throughput, and therefore the examination costs. In order to increase the number of patients who can be helped with an MR examination, and given the background of increasing costs in health care systems, an aging population in the highly industrialized nations and the desire to also make magnetic resonance imaging accessible to people in less highly developed countries, this is also an important aspect for the acceleration of the individual measurements.

The measurement time per measurement protocol could already be drastically reduced in part with the integration of fast sequence techniques—such as "Turbo Spin Echo" (TSE) sequences or, respectively, "Fast Spin Echo" (FSE) or "Echoplanar Imaging" (EPI)—and what are known as parallel acquisition techniques into the clinical routine. An example of an FSE sequence is described in U.S. Pat. No. 6,771,069 B2.

TSE sequences use an RF excitation pulse, followed a series of RF refocusing pulses. The spin echo arising after each refocusing pulse is normally individually phase-coded, such that multiple k-space lines can be acquired per excitation, and thus the acquisition time is reduced relative to classical spin echo sequences. The TSE technique and the FSE technique are especially important in clinical diagnostics—in particular for the T2 contrast—due to its relative insensitivity with regard to off-resonance (i.e. a deviation from the Larmor frequency), which can occur, for example, as a result of system imperfections, magnetic susceptibility variations of the tissue, metallic implants, etc. For special variants of these sequences, separate acronyms are used, such as "Rapid Acquisition with Relaxation Enhancement" (RARE), "Half-Fourier Acquired Single-shot Turbo Spin Echo" (HASTE) and "Periodically Rotated Overlapping Parallel Lines with Enhanced Reconstruction" (PROPELLER), which is explained below. A TSE sequence technique, however, is a relatively slow sequence technique in comparison to EPI techniques and is characterized by high radio-frequency radiation into the patients due to the large number of refocusing pulses. The specific absorption rate (SAR)—thus the radio-frequency energy that is absorbed in a defined time interval per kg of body weight—is regulated.

This has the effect that the acquisition time of a TSE sequence—in particular at field strengths of 3 Tesla or more—is normally not limited by the capacity of the MR system (for example the gradient system) but rather by the specific absorption rate. In systems known as ultra-high field systems with field strengths of 7T and beyond, an examination with a TSE sequence—with a slice count sufficient for the coverage of the anatomy to be examined and in a clinically acceptable measurement time—has previously not been possible due to the associated SAR exposure.

In order to achieve an additional acceleration, in a relatively new group of acceleration techniques (SMA—"Simultaneous Multi-Slice Acquisition") that have not yet become established in clinical practice. In such techniques, it is sought to excite multiple slices of a slice stack either simultaneously (by means of "wideband MRI") or in a short time series (designated as "Simultaneous Echo Refocusing"), and then either to separate the signal emitted from the different slices as a result of this excitation into readout windows in (close) chronological succession or to simultaneously receive said signal and subsequently separate it via suitable post-processing methods (in "post-processing").

In principle, it would be desirable to also excite multiple slices of a slice stack simultaneously or in a short chronological series, and to simultaneously refocus them repeatedly within the scope of a TSE sequence technique, as mentioned above. Due to the cited SAR problem, however, such a new TSE sequence technique with a simultaneous acquisition of multiple slices will then only be able to shorten the actual examination duration when the radio-frequency radiation at least does not increase per time period. This fact makes a series of new SMA techniques for TSE sequences practically irrelevant. An additional difficulty in the design of such novel TSE sequences is the fact that the refocusing pulses are normally not perfect 180° pulses. An inherent, unavoidable reason for this is that the slice profile is not exactly rectangular (due to the finite duration of the RF pulses), and thus deviates from the ideal 180° at least at the slice edges.

As a result, the "refocusing pulse" only partially refocuses the existing transversal magnetization, flips a portion of the remaining, unfocused magnetization back in the longitudinal axis, and leaves the rest unaffected. The longitudinal magnetization (i.e. the magnetization proceeding in the direction of the basic magnetic field) that is present before the "refocusing pulse" is accordingly partially "excited", partially inverted and partially left unaffected in the transverse plane. The transverse magnetization that is present after the "refocusing pulse" (i.e. the spins that are currently excited) then accumulates as a result of the switched gradient fields and/or a phase portion accumulates as a result of unwanted, off-resonances that may be present, while the longitudinal magnetization is unaffected by the switched gradient fields and is subject only to the relatively slow T1 decay until it is flipped back by one of the following "refocusing pulses" in the transversal plane.

Each "refocusing pulse" thus acts as an inversion pulse for one portion of the spins; as an excitation pulse for a different portion; as a "restore pulse" (which flips the spins back in the longitudinal direction, wherein the current phase positions of the spins is maintained) for an additional portion; and is transparent for the remainder. Spins on which each "refocusing pulse" acts similarly follow what is known as a coherent echo path. The number of different coherent echo paths increases exponentially with the number of refocusing pulses. Spins that result from different coherent echo paths normally contribute to a signal that is acquired as of the second "refocusing pulse" in a readout window. If these spins accumulate along the different coherent echo paths of different phase portions, this leads to destructive interference. The signal collapses; the images calculated from the raw data show shadows and a poor signal-to-noise ratio (SNR); and the pulse sequence is not able to maintain a long echo train. The latter is a requirement for the T2 contrast (which is particularly important in connection with the TSE imaging) and the efficiency increase, which can be achieved relative to a spin echo sequence.

In order to ensure that only those coherent echo paths along which the spins accumulate the same phase portions contribute to the signal in each readout window, in the article "Simultaneous Spin-Echo Refocusing" in Magnetic Resonance in Medicine, 54, 2005, P. 513-523 by M. Günther and D. A. Feinberg, and in U.S. Pat. No. 6,853,188 B2, a TSE sequence is described in which m adjacent slices are excited in short time intervals and respective echoes of the m slices are refocused with a series of refocusing pulses. With a specific scheme with spoiler gradient pulses, echoes whose signal is emitted by spins of different slices are prevented from undesirably coinciding in a readout window. This spoiler scheme dephases signals of those spins that follow specific, coherent echo paths. The simultaneous refocusing of the m slices causes the radiated radio-frequency energy to be reduced by approximately a factor of m. However, due to the spoiling of specific, coherent echo paths, the signal linked with these echo paths cannot be used for imaging, which leads to an SNR loss relative to the separate acquisition of the slices. In addition, in this pulse sequence it is unfortunately not possible to maintain a long echo time (for example with more than 20 echoes). Therefore, the pulse sequence cannot be used for T2-weighted imaging.

Therefore, in EP 2 239 592 A1 a RARE sequence is proposed in which the refocusing of multiple excited slices is achieved separately by slice-selective refocusing pulses in short succession. Particularly when a larger number of slices should be excited simultaneously, this separate refocusing leads to a not-insignificant lengthening of the sequence.

SUMMARY OF THE INVENTION

An object of the present invention is to provide a suitable method for operation of a magnetic resonance tomography system; a corresponding pulse sequence; and a control device for a magnetic resonance tomography system, in which the aforementioned problem is avoided.

In the method according to the invention, at least the following method steps are implemented within the scope of a sequence module:

A series of spatially selected RF slice excitation pulses is initially emitted in order to achieve an excitation of a plurality m (i.e. at least two) of slices in the examination subject that are normally directly adjacent. A slice is thereby respectively excited via an RF slice excitation pulse of this pulse series, wherein successive RF slice excitation pulses are respectively situated at a first time interval from one another. As is known to those skilled in the art, the spatial selectivity of the RF slice excitation pulses hereby results via application of a parallel slice-selection gradient, i.e. by temporally matching parallel switching of slice-selection gradient pulses. In the following the terms "application of gradients" and "switching of gradient pulses" are used synonymously.

A first RF refocusing pulse is then emitted at a second time interval after the first excitation pulse, or alternatively after the last excitation pulse of the series of RF slice excitation pulses. Moreover, as a result at least one additional RF refocusing pulse is respectively emitted at a third time interval after a preceding RF refocusing pulse, wherein the third time interval is twice as long as the second time interval. The spatial width of the RF refocusing pulses to generate a plurality of time-separated echo signals per RF refocusing pulse is selected such that the RF refocusing pulses ($\beta_1$, $\beta_2$, $\beta_3$) for simultaneous refocusing of all excited slices acquire or, respectively, include at least a portion of an excitation volume of all excited slices, meaning that each of the excited slices acts on at least a portion of an excitation volume. The spatial width—i.e. the slice width—of the RF refocusing pulses is thereby adjustable via temporally matching switching of suitable gradient pulses in the slice selection direction, as in the RF slice excitation pulses.

The number of echo signals per RF refocusing pulse thereby corresponds to at least the number of excited slices, and at most to double the number of excited slices minus 1 (meaning that the number of echo signals is at least m and at most 2m−1), wherein the echo signals associated with (following) an RF refocusing pulse are situated at an interval from one another that corresponds to the first time interval.

An additional gradient is switched in the slice-selection gradient between the slice-selection gradients of two successive RF slice excitation pulses, this additional gradient ensuring that the accumulated 0th moment between the isodelay points of the two RF slice excitation pulses in the slice selection direction is zero.

A pulse sequence according to the invention for the control of a magnetic resonance system to generate magnetic resonance image data of an examination subject has at least one sequence module that includes at least the pulses or the pulse series explained above. A sequence module means a self-contained part of a pulse sequence that leads to an echo train with a defined number of echo signals, meaning that a sequence module includes an excitation part with the radio-frequency pulses and gradient pulses that are emitted or applied during the initial excitation of all participating slices, as well as the subsequent echo train with the refocusing pulses, gradient pulses, echo signals and readout windows. A pulse sequence accordingly includes one or more such sequence modules per m slices.

A TSE pulse sequence with which m different slices can be excited, and the signal emitted by these m slices can subsequently be simultaneously refocused with a series of refocusing pulses, is thus provided by the invention, wherein the echo signals of the m slices that are created after each of these refocusing pulses can be acquired in temporally separate readout windows. By the simultaneous refocusing, the radio-frequency energy that is accumulated via the refocusing pulses is thereby reduced by approximately a factor of m relative to the separate acquisition of the m slices (with corresponding refocusing pulses and flip angles). It is thus possible to reduce the examination duration of a SAR-limited measurement at a given resolution by approximately a factor of m relative to the prior art. Alternatively, a higher resolution can be achieved in a given examination duration.

The relative time spacing of the excitation pulses and RF refocusing pulses and the switching of gradient pulses according to the invention that are described above ensure that the echoes of different slices form at different times, and thus can be read out in different, temporally separate readout windows. Furthermore, the signals of different echo paths of a slice are split up into up to two groups via the temporal arrangement of the RF pulses and the switching of the gradient fields, such that echoes belonging to different groups form with temporal separation and can be read out in different readout windows that also do not coincide with the readout windows of the other slices.

In contrast to the pulse sequence from Günther and Feinberg that is described above, via this measure a spoiling of specific coherent echo paths can be omitted, and therefore the signal linked with these echo paths can be used for imaging. In particular, a destructive interference between signals of spins that follow different coherent echo paths during a very long echo train (with 15 or more refocusing pulses) is thereby avoided. The sequence is therefore compatible with all common TSE contrasts—in particular the particularly important T2 contrast.

A control device of the aforementioned type according to the invention must be designed such that it controls the magnetic resonance tomography system in operation to generate magnetic resonance image data of an examination subject by means of a pulse sequence according to the invention that is described above.

A magnetic resonance tomography system according to the invention includes the following components:

a basic field magnet system in order to apply a homogeneous basic magnetic field in a measurement space in which the examination subject is located;

an RF transmission antenna system in order to emit the radio-frequency pulses into the examination subject;

a gradient system in order to apply additional, time-limited gradient fields by switching of gradient pulses, as described above; and an RF reception antenna system in order to acquire the magnetic resonance signals from the examination subject. The RF transmission antenna system and the RF reception antenna system can thereby be different antenna systems or the same antenna system.

Furthermore, the magnetic resonance tomography system requires an aforementioned control device according to the invention that controls the basic field magnet system, the RF transmission antenna system, the gradient system and the RF reception antenna system during operation for generation of magnetic resonance slice acquisitions of an examination subject. For example, for this purpose, the control device can have various sub-components such as a radio-frequency transmission device to send radio-frequency pulses to the RF transmission antenna system, a gradient system interface to control the gradient system, a radio-frequency reception device to generate the raw data from the signals received via the RF reception antenna system, and a sequence control unit that forwards measurement sequence control data to the radio-frequency transmission device, the gradient system interface and the radio-frequency reception device during operation to generate the magnetic resonance exposures; such that this data control the RF transmission antenna system, the gradient system, the radio-frequency reception device and the RF reception antenna system in the manner according to the invention, for example to acquire the raw data for a stack of slices.

Significant parts of the control device are preferably realized in the form of software at a suitable programmable control device with corresponding storage capabilities. This in particular pertains to the sequence control unit. The radio-frequency transmission device, the gradient system interface and the radio-frequency reception device can also be realized at least in part in the form of software units, wherein other units of these components are again purely hardware units (for example the radio-frequency amplifier, the radio-frequency transmission device, a gradient pulse generation device of the gradient system interface, or an analog/digital converter of the radio-frequency reception device etc.). A realization largely in software—in particular of the sequence control unit—has the advantage that even magnetic resonance system control devices that have already previously been in use can be retrofitted in a simple manner via a software update in order to operate in the manner according to the invention.

The above object is also achieved by a non-transitory, computer-readable data storage medium, such as a portable memory and/or transfer via a network, which causes programming instructions to be loaded directly into a memory of a programmable control device, with program segments in order to execute all steps of the method according to the invention when the program is executed in the control devices.

As explained above, up to 2m−1 subsequent echo signals are generated per RF refocusing pulse given m simultaneously excited slices. After the first RF refocusing pulse, precisely m echo signals thereby initially occur, i.e. as many echo signals as slices that have been excited. The first RF refocusing pulse is thus designed so that a respective echo signal is formed for each of the excited slices. As mentioned, the time interval of two echo signals is thereby equal to the first time interval, i.e. the time interval of the excitation of the slices. 2m−1 echo signals then come after every additional RF refocusing pulse. This means that the additional RF refocusing pulses are thus designed and chronologically arranged in the sequence so that a number of temporally separate echo signals is respectively formed that is one less than double the number of excited slices. The echo signals occurring after an RF refocusing pulse are then respectively, advantageously read out in a number of readout windows (corresponding to the echo count) under application of a gradient field via switching of a gradient pulse series with one or more gradient pulses in the readout direction. In a preferred variant of the invention, for this a respective gradient pulse series is already respectively switched between two successive RF slice excitation pulses in a readout direction, the 0th moment of which respective gradient pulse series is equal to the accumulated 0th moment of a gradient pulse series in the readout direction that is switched later between two successive echo signals. As is known to those skilled in the art, the 0th moment (also just called "moment" in the following) of a gradient pulse corresponds to the area under the pulse, i.e. to the amplitude of the gradient, integrated over time.

Via these gradient pulses in the readout direction between the RF slice excitation pulses with the matching moment, it is achieved that the 0th moment is respectively always equal to zero at the different echo points in time. In spite of multiple excited slices and splitting into different readout windows, it is thereby possible to place a readout gradient for spatial coding, and thus to respectively acquire the echo signal not only integrally but rather with spatial resolution.

Moreover, it is preferably ensured that a moment that is acquired between the last excitation pulse of the series of RF slice excitation pulses and the first RF refocusing pulse as a result of a switched gradient pulse in the readout direction is equal to the moment that is accumulated in the readout direction between the first RF refocusing pulse and a first echo. Via such a readout pre-phasing gradient pulse between last excitation pulse and refocusing pulse, it can be ensured that the total moment at the point in time of the first echo signal is zero.

The pulse sequence is advantageously designed so that the accumulated 0th moment of all gradient pulses that are switched between the isodelay points of two successive RF slice excitation pulses in a slice selection direction is also zero. The isodelay point of an RF slice excitation pulse is the point in time within the radiation time of the excitation pulse as of which the spins can be observed to be located in the transversal plane. For example, the time between the isodelay point of the RF excitation pulse and the end of the RF excitation pulse serves to calculate the moment of a slice refocusing gradient. This slice refocusing gradient has the opposite algebraic sign as the slice selection gradient. It is switched after the end of the RF radiation and serves to compensate for a phase dispersion along the slice as a result of the slice excitation gradient. In general, the isodelay point coincides with the peak of the RF pulse, thus in good approximation with the middle of the RF pulse given symmetrical SINC pulses.

In a preferred embodiment of the pulse sequence according to the invention, the time duration of an RF slice excitation pulse is shorter than the time duration of an RF refocusing pulse. As is explained below, the shorter the duration of an excitation pulse, the greater the readout gradient that can be chosen. With increase of the readout gradient, k-space to be acquired is traversed in the readout direction in a shorter amount of time, such that a relatively short echo interval can still be realized in spite of the multiple readout windows per refocusing pulse. This can lead to an improvement of the image quality.

Depending on the more precise embodiment of the pulse sequence, there are various possibilities of how the raw data required for the image reconstruction of a slice are acquired in k-space.

In a first alternative, k-spaces of the slices that are to be sampled are respectively acquired once or twice in a single echo train of a sequence module. This means that all required raw data are respectively completely acquired in a single sequence module of the pulse sequence for every single slice. A one-time acquisition thereby takes place for those slices whose echo paths are not split up (as is explained below), meaning that their raw data are acquired in only a single readout window. A two-time acquisition takes place for all other respective slices.

In a second alternative, k-space of the individual slices that is to be scanned is respectively acquired in a pulse sequence with multiple sequence modules, wherein raw data of one or two segments per slice are acquired with each sequence module (i.e. with each echo train) on the basis of the echo signals.

The segmentation of k-space can take according to a PROPELLER trajectory, for example. For this purpose, in each echo train raw data are advantageously acquired from one or two Cartesian k-space segments (meaning that the readout points of each propeller blade lie on the grid points of a Cartesian grid) per slice that respectively include the k-space center.

In an acquisition of raw data from different k-space segments of a specific slice in various sequence modules, the time position of the RF slice excitation pulse of this slice is particularly preferably varied from pulse sequence to pulse sequence. Contrast and SNR differences of various slices can be reduced or even avoided entirely, which can occur in that the echo paths of only a few slices are not split up in the raw data acquisition, and the echo paths of the other slices are split up. For example, the cited signal differences can be avoided in the PROPELLER variant in that every m-th k-space segment of each slice is acquired in a mode in which the echo paths are not split up. However, the principle functions independently of whether it is a PROPELLER sequence or not.

In the method according to the invention, the raw data necessary for image reconstruction are acquired separately, multiple times in different readout windows for at least some slices. Various methods according to the invention are provided for a generation of magnetic resonance image data on the basis of such raw data that were acquired multiple times in different readout windows using a method according to the invention within the scope of a sequence module.

In a first variant, a calculation of separate magnitude images initially takes place for the raw data from the different readout windows. A combination of magnitude images that are associated with the same slice into a single slice image of this slice then subsequently takes place to improve the signal-to-noise ratio. The combination of the magnitude images of the same slice advantageously takes place with the use of a sum-of-squares method.

In a second variant, a complex-value combination of image data of a specific slice whose raw data were acquired in various readout windows with a single echo train takes place in a second variant. This complex-value combination advantageously takes place after the phase—which spatially varies slowly in image space—was removed via computation. Alternatively, instead of the computer elimination of the phase that spatially varies slowly in image space a different method can also be used that avoids the destructive interference of the signals from different readout windows.

Exemplary embodiments for both variants are explained later in more detail using Figures. This specific reconstruction of the image data on the basis of the raw data can take place immediately in a reconstruction device of the magnetic resonance tomography system, for example in its control device. In principle, however, such a reconstruction can also be implemented at a different computer. It is only necessary that corresponding raw data are provided in some manner via an interface on a network to which the magnetic resonance tomography system is also connected.

BRIEF DESCRIPTION OF THE DRAWINGS

FIG. 11 shows further enlargements of the exemplary slice images of FIG. 9.

DESCRIPTION OF THE PREFERRED EMBODIMENTS

Figure 1:
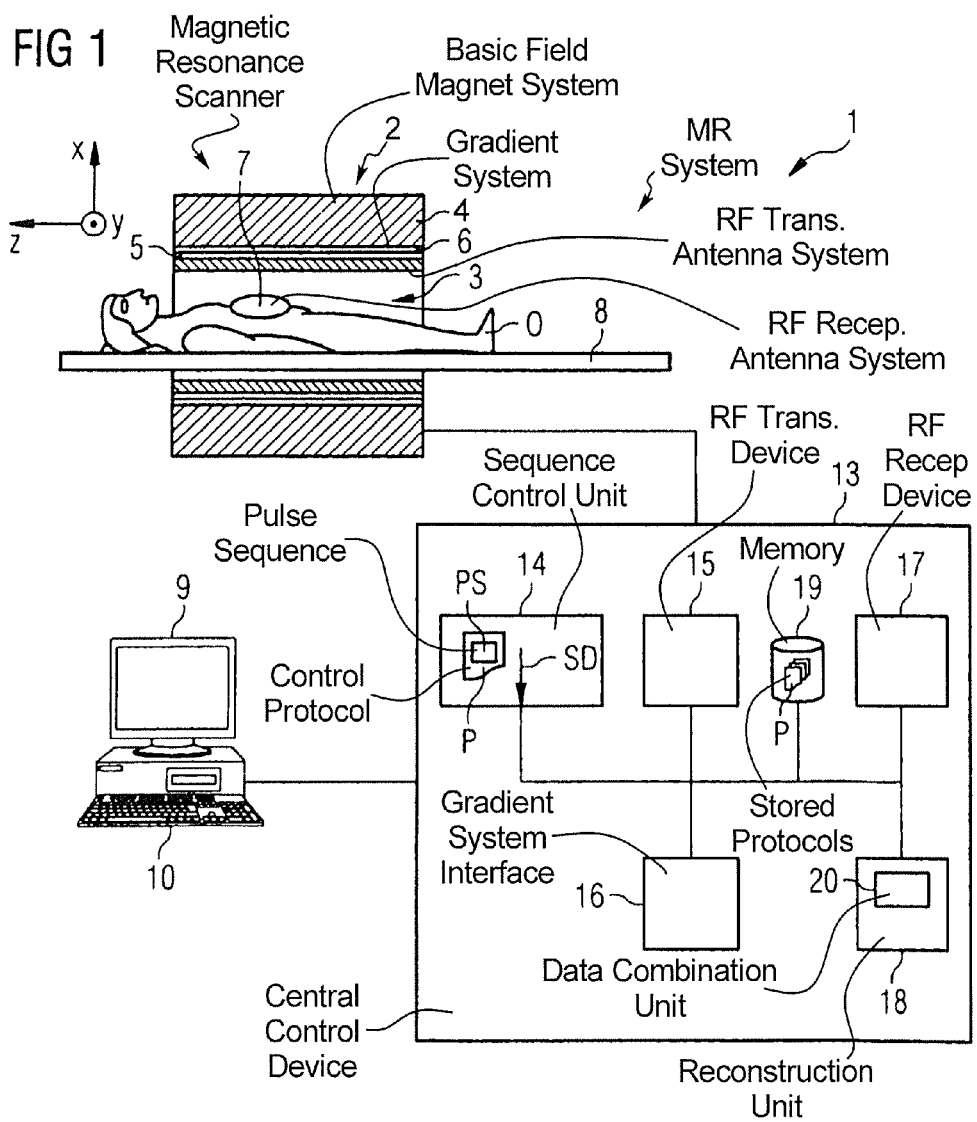
FIG. 1 is a schematic representation of a magnetic resonance tomography system according to an exemplary embodiment of the invention.

A magnetic resonance tomography system 1 (also shortened to "MR system" in the following) according to the invention is schematically presented in FIG. 1. They system includes the actual magnetic resonance scanner 2 with an examination space 3 or patient tunnel into which an examination subject O on a bed 8 can be moved. Here, the subject O is a patient or test subject in whose body the examination subject—a specific organ, for example—is located) on a bed 8 can be driven.

The magnetic resonance scanner 2 is typically equipped with a basic field magnet system 4, a gradient system 6 and an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 includes local coils (symbolized by only a single local coil in FIG. 1) to be arranged on the patient or test subject. In principle the whole-body coil can also be used as an RF reception antenna system and the local coils can be used as an RF transmission antenna system insofar as these coils can respectively be switched into different operating modes. Here the basic field magnet system 4 is typically designed so that it generates a basic magnetic field in the longitudinal of the patient, i.e. the longitudinal axis of the magnetic resonance scanner 2 that runs along the z-direction. The gradient system 6 typically is composed of individually controllable gradient coils in order to be able to switch gradients in the x-, y- or z-directions, independently of one another.

The MR system shown in FIG. 1 is a whole-body system with a patient tunnel into which a patient can be completely introduced. In principle, however, the invention can also be used in other MR systems, for example with laterally open, C-shaped housing, but also in particular with smaller magnetic resonance scanners in which only a body part can be positioned, for example.

Furthermore, the MR system 1 has a central control device 13 that is used to control the MR system 1. This central control device 13 comprises a sequence control unit 14 for measurement sequence control. With this the series of radio-frequency pulses (RF pulses) and gradient pulses is controlled within a measurement session depending on a selected pulse sequence PS or a series of multiple pulse sequences to acquire multiple slices in a volume region of interest of the examination subject. For example, such a pulse sequence PS can be provided and parameterized within a measurement or control protocol P. Various control protocols P for different measurements or, respectively, measurement sessions are typically stored in a memory 19 and can be selected by an operator (and possibly changed as necessary) and then be used to implement the measurement. In the present case, the control device 13 includes—among other things—pulse sequences that operate according to the method according to the invention. Examples of such pulse sequences are explained in detail later using FIGS. 3 through 5 and 7.

To output the individual RF pulses of a pulse sequence PS, the central control device 13 has a radio-frequency transmission device 15 that generates and amplifies the RF pulses and feeds them into the RF transmission antenna system 5 via a suitable interface (not shown in detail). The control device 13 has a gradient system interface 16 to control the gradient coils of the gradient system 6 in order to suitably switch the gradient pulses corresponding to the predetermined pulse sequence. The sequence control unit 14 communicates with the radio-frequency transmission device 15 and the gradient system interface 16 in a suitable manner (for example via emission of sequence control data SD) to execute the pulse sequences. The control device 13 has a radio-frequency reception device 17 (likewise communicating with the sequence control unit 14 in a suitable manner) in order to receive magnetic resonance signals—the echo signals explained later within the scope of the present invention—in a coordinated manner by means of the RF reception antenna system 7 within the readout window provided by the pulse sequence PS, and thus to acquire the raw data for the individual slices.

A reconstruction unit 18 accepts the acquired raw data and reconstructs magnetic resonance image data for the slices from these. This reconstruction also normally takes place on the basis of parameters that are provided in the respective measurement protocol. For example, these image data can then be stored in a memory 19. In the present case, the reconstruction unit 18 is designed so that it can operate according to the method according to the invention as it is explained as an example later using FIGS. 6 and 8. In particular, the raw data and/or image data of a slice can thereby be combined in a special data combination unit 20 of the reconstruction unit 18.

Operation of the central control device 13 can take place via a terminal with an input unit 10 and a display unit 9 via which the entire MR system 1 can thus also be operated by an operator. MR images can also be displayed at the display unit 9, and measurements can be planned and started by means of the input unit 10 (possibly in combination with the display unit 9), and in particular control protocols P can be selected with suitable pulse sequences PS as explained above and can possibly be modified.

The MR system 1 according to the invention, and in particular the control device 13, can also have a number of additional components that are not shown in detail but are typically present at such systems, for example a network interface in order to connect the entire system with a network and be able to exchange raw data and/or image data or parameter maps, but also additional data, for example patient-relevant data or control protocols.

The manner by which suitable raw data can be acquired and MR images can be reconstructed from these by a radiation of RF pulses and the switching of gradient pulses is known in principle to those skilled in the art, and thus need not be explained in detail herein. The most varied slice measurement sequences—for example in particular the TSE pulse sequences that have already been explained above—are likewise fundamentally known to those skilled in the art. Nevertheless, in the following a typical conventional TSE sequence is initially explained using FIG. 2 in order to clarify the differences relative to a pulse sequence according to the invention that is explained later using examples shown in FIGS. 3 through 5 and 7. The arrangement of the RF and gradient pulses, magnetic resonance signals (echo signals) and readout windows over time (from left to right) is respectively shown in a typical manner on different axes in the pulse diagrams of FIGS. 2 through 5. The RF pulses and echo signals are displayed on the uppermost axis; the gradient pulses in the slice selection direction are displayed on the second axis; the gradient pulses in the readout direction are displayed on the third axis; the gradient pulses in the phase coding direction are displayed on the fourth axis; and the readout windows are displayed on the lowermost axis. The following applies for the three gradient axes. The horizontal axis (drawn with a dashed line) is respectively the zero line. The level of the signals respectively represents the relative amplitude (not necessarily to scale). The algebraic sign of the amplitude (relative to the zero axis) corresponds to the direction of the gradient field. The gradient pulses (dashed lines) in Figures are partially populated with one or more capital letters. These letters stand for the 0th moment of a gradient pulse or, respectively, the 0th moment accumulated during a time interval from the gradient pulse. This moment information serves to facilitate the understanding of the pulse sequence. In particular, different gradient pulses or partial intervals of different gradient pulses that accumulate the same 0th moment are populated with the same capital letters.

Figure 2:
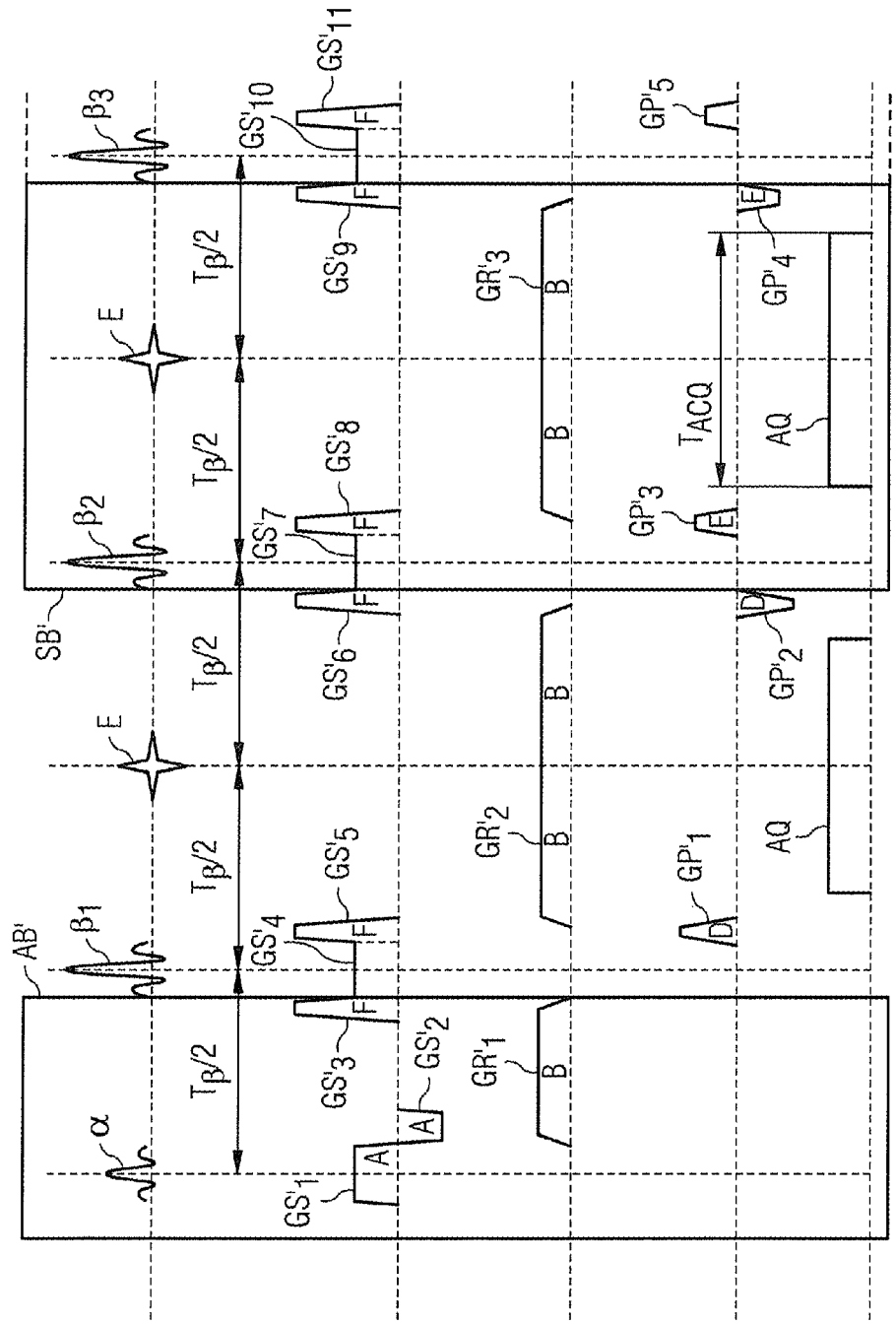
FIG. 2 shows a pulse scheme for a possible workflow of a conventional single slice TSE pulse sequence in the prior art.

FIG. 2 shows the first two echoes E of a conventional TSE sequence in the prior art. The sequence starts with a slice-selective 90° RF slice excitation pulse α(shortened to "excitation pulse" in the following), followed by a series of slice-selective RF refocusing pulses $\beta_1$, $\beta_2$, $\beta_3$ (shortened to "refocusing pulse" in the following). After each refocusing pulse $\beta_1$, $\beta_2$, $\beta_3$, precisely one echo is thereby formed that is read out in a respective readout window (readout interval) AQ. The duration $T_{ACQ}$ of the readout window AQ is thereby determined by the number of read out data points and the time interval of two data points, what is known as the "dwell time". Only three refocusing pulses $\beta_1$, $\beta_2$, $\beta_3$ are shown in FIG. 2; in T2-weighted imaging (in the also pulse sequences according to the invention that are presented later) the number is normally significantly greater, and varies (depending on the application) between ten and multiple hundreds of refocusing pulses. The number of refocusing pulses is also called echo train length (abbreviated to ETL).

The shown sequence satisfies a condition known as the Carr-Purcell-Meiboom-Gill condition (CPMG condition), which ensures that echo signals E of spins that follow different coherent echo paths constructively superimpose at the echo point in time. Among other things, the CPMG condition requires that the phase that a spin acquires between two arbitrary successive refocusing pulses $\beta_1$, $\beta_2$, $\beta_3$ must respectively be the same. For example, the CPMG condition is explained in more detail in the "Handbook of MRI Pulse Sequences", Elsevier Academic Press; Edition: illustrated edition (21 Sep. 2004); ISBN-10: 0120928612; ISBN-13: 978-0120928613 by Matt A. Bernstein, Kevin E. King, Xiaohong Joe Zhou.

First, for this the time interval $T_{\beta'}$ between the $\beta_1$, $\beta_2$, $\beta_3$ is chosen to be twice as long as the time interval between the isodelay point of the excitation pulse and the middle of the first refocusing pulse $\beta_1$.

Second, the phase of the refocusing pulses is rotated by 90° relative to the phase of the excitation pulses, meaning that the $B_1$ field of the refocusing pulses is applied in parallel or antiparallel to the y-axis when the $B_1$ field of the excitation pulse is applied along the x-axis in a coordinate system rotating around the z-axis in which the $B_0$ field, for example.

In both the excitation pulse α and the refocusing pulses $\beta_1$, $\beta_2$, $\beta_3$, the width of the excited slice is respectively regulated via the bandwidth of the RF pulse and via a slice selection gradient pulse $GS'_1$, $GS'_4$, $GS'_7$, $GS'_{10}$ that is applied during the radiation of the excitation or refocusing pulse $\beta_1$, $\beta_2$, $\beta_3$. Pulses each known as a spoiler gradient $GS'_3$, $GS'_5$, $GS'_6$, $GS'_8$, $GS'_9$, $GS'_{11}$ are respectively switched (activated) immediately before and immediately after each refocusing pulse $\beta$, the object of which is to dephase the FID of the refocusing pulse $\beta_1$, $\beta_2$, $\beta_3$ before the following readout window AQ so that it does not deliver a signal contribution. FID ("free induction decay") thereby designates the transient signal of a spin system that is induced by a single RF pulse. In other words, it is the signal that emanates from spins for which the refocusing pulse "acts" as an excitation pulse.

The left and right spoiler gradients $GS'_3$, $GS'_5$ should have the same 0th moment. In the figures, the absolute value of the moment of a gradient pulse (which corresponds to the area under the pulse, i.e. the amplitude in the gradient integrated over time) is respectively symbolized by capital letters in the appertaining surface area of the pulse. The reference characters F in FIG. 1 thus show that the left and right spoiler gradient $GS'_3$, $GS'_5$ have the same moment. Furthermore, the spoiler gradients $GS'_3$, $GS'_5$, $GS'_6$, $GS'_8$, $GS'_9$, $GS'_{11}$ of different refocusing pulses $\beta_1$, $\beta_2$, $\beta_3$ again also have the same moment F. Every other choice already violates the CPMG condition.

After the excitation pulse $\alpha$, a slice rephasing gradient pulse $GS'_2$ is required whose moment $-A$ is equal to the negative of the moment A accumulated by the slice-selection gradient pulse $GS'_1$ between the isodelay point in time of the excitation pulse $\alpha$ and the end of the slice-selection gradient pulse $GS'_1$.

The chronological arrangement of the RF pulses is such that a spin echo signal forms at the point in time $T_\beta/2$ after each refocusing pulse $\alpha$.

This is respectively frequency-coded by a readout gradient pulse $GR'_2$, $GR'_3$. A readout pre-phasing gradient pulse $GR'_1$ between excitation pulse $\alpha$ and the first refocusing pulse $\beta_1$, whose moment B coincides with the moment B that a spin accumulates from the beginning of the readout gradient pulse $GR'_2$, $GR'_3$ up to the center of the echo signal E, ensures that the total moment is zero at the point in time of the echo signal E.

The second part of the readout gradient $GR'_2$, $GR'_3$ after the echo likewise has the area B, and therefore also serves as a pre-phasing gradient for spins that follow coherent echo paths that are located between more than one pair of refocusing pulses $\beta_1$, $\beta_2$, $\beta_3$ in the transversal plane.

A phase coding gradient pulse $GP'_1$, $GP'_3$ serves for phase coding of the echo signal E, which phase coding gradient $GP'_1$, $GP'_3$ is respectively switched between the end of the refocusing pulse $\beta_1$, $\beta_2$, $\beta_3$ and the beginning of the readout window AQ'. The moment D, E acquired via this gradient pulse $GP'_1$, $GP'_3$ must be compensated after the end of the readout interval AQ and before the beginning of the next refocusing pulse $\beta_2$, $\beta_3$ via a phase refocusing gradient pulse $GP'_2$, $GP'_4$ in the phase coding direction with a moment $-D$, $-E$ in order to satisfy the cited CPMG condition.

For graphical reasons, only the first two echo signals E are shown in FIG. 2. Via repetition of the framed sequence block SB', the sequence diagram is obtained for the complete sequence module which comprises the excitation block AB' with the excitation pulse $\alpha$ and the subsequent echo train. The echo train is composed of multiple sequence blocks SB' switched in series. Each sequence block SB' includes: a refocusing pulse with subsequent echo signals E; a slice-selection gradient; the right spoiler gradient of the separate refocusing pulse and the left spoiler gradient of the next refocusing pulse; a readout gradient; a readout interval AQ; a phase coding gradient; and a phase refocusing gradient matching this. If different echo signals E code different k-space lines, the moment of the phase coding gradient $GP'_1$, $GP'_3$ and of the phase coding refocusing gradient $GP'_2$, $GP'_4$ is thus varied between the repetitions of the sequence block SB'. All other gradient pulses do not change their value in order to not infringe on the CPMG condition.

Figure 3:
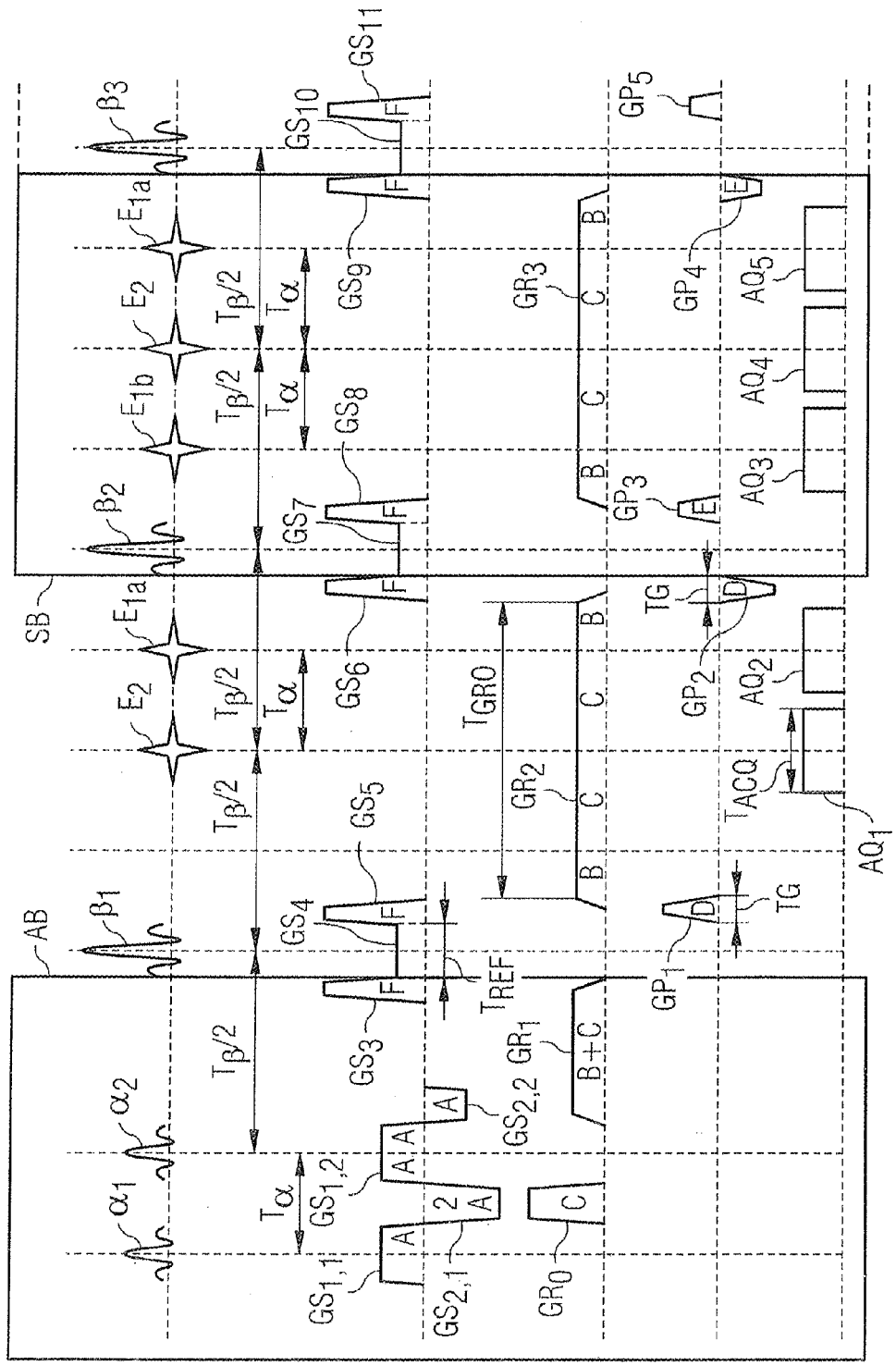
FIG. 3 shows a pulse scheme for a multislice TSE pulse sequence according to a first exemplary embodiment of the invention, with two simultaneously refocused slices.

FIG. 3 shows the start of a pulse sequence for simultaneous refocusing of multiple excited slices according to a first embodiment of the invention. For the sake of a better presentation, here only the excitation and simultaneous refocusing of m=2 slices is shown; however, the sequence can be used for the simultaneous refocusing of more than two slices (meaning that m>2) without further measures. Assuming the conventional TSE sequence according to FIG. 2, the following changes must be made in order to arrive at such a pulse sequence according to the invention:

Instead of only one slice excitation pulse $\alpha$, two slice excitation pulses $\alpha_1$, $\alpha_2$ are now emitted at a time interval $T_\alpha$ from one another within the excitation block AB. The two slice excitation pulses $\alpha_1$, $\alpha_2$ excite the spins in different slices parallel to one another. If thicknesses of the slices and the radio-frequency bandwidth of the two slice excitation pulses $\alpha_1$, $\alpha_2$ coincide, they this differ only in their carrier frequency. The duration of the time interval $T_\alpha$ between the slice excitation pulses $\alpha_1$, $\alpha_2$ is discussed in further detail in the following.

Moreover, the width of the refocusing pulses $\beta_1$, $\beta_2$, $\beta_3$ is extended such that they respectively comprise both the slice excited by the excitation pulse $\alpha_1$ and the slice excited by the excitation pulse $\alpha_2$. If $\Delta d$ designates the thickness of an excited slice and if d is the interval of the two slices, the width of the slice achieved via a refocusing pulses $\beta_1$, $\beta_2$, $\beta_3$ is thus chosen to be at least $d+\Delta z$ (or, given m slices, in a more general form $(m-1) \cdot d+\Delta z$). If the radio-frequency bandwidth of the refocusing pulses $\beta_1$, $\beta_2$, $\beta_3$ from the sequence according to FIG. 2 is maintained, this can be achieved in that—for example—the amplitude of the respective slice-selection gradient pulse $GS_4$, $GS_7$ that is emitted with the refocusing pulses $\beta_1$, $\beta_2$, $\beta_3$ is reduced relative to the slice-selection gradient pulse $GS'_4$, $GS'_7$. The carrier frequency of the refocusing pulses $\beta_1$, $\beta_2$, $\beta_3$ is also respectively selected such that the center of the refocused slice is situated precisely in the middle of the m excited parallel slices. The spoiler gradient pulses $GS_3$, $GS_5$, $GS_6$, $GS_8$, $GS_9$, $GS_{11}$ do not need to be adapted.

While precisely one echo signal is formed after each refocusing pulse $\beta_1$, $\beta_2$, $\beta_3$ in the conventional pulse sequence according to FIG. 2, the sequence according to the invention generates up to $2m-1$ echo signals $E_2$, $E_{1a}$, $E_{1b}$ after each refocusing pulse, wherein m is the number of simultaneously refocused slices. The time interval $T_\alpha$ between two successive echo signals $E_2$, $E_{1a}$, $E_{1b}$ is thereby equal to the time interval $T_\alpha$ of the excitation pulses. If all readout parameters of the pulse sequence from FIG. 2—and thus also the readout duration $T_{ACQ}$—were maintained, the time interval $T_\beta$ between two refocusing pulses $\beta_1$, $\beta_2$, $\beta_3$ would need to be adapted accordingly. Alternatively, the readout duration $T_{ACQ}$ of the readout window can also be shortened, for example in that the dwell time is shortened by a factor of x. Given an unmodified field of view (FoV) and count of the read-out data points, this means that the amplitude of the readout gradient pulses $GR_2$, $GR_3$ would need to be increased by a factor of x relative to the readout gradient pulses $GR'_2$, $GR'_3$ according to FIG. 1 so that the k-space interval of the readout points remains unchanged. This factor x is thereby limited by the maximum gradient amplitude of the gradient system and the minimum dwell time of the analog/digital converter.

In order to avoid the overlapping of the different readout windows $AQ_1$, $AQ_2$, $AQ_3$, $AQ_4$, $AQ_5$ for the different echo signals $E_2$, $E_{1a}$, $E_{1b}$, the time interval $T_\alpha$ between two successive echo signals $E_2$, $E_{1a}$, $E_{1b}$ is limited at the lower bound with the establishment of the duration $T_{ACQ}$ of the readout windows $AQ_1$, $AQ_2$, $AQ_3$, $AQ_4$, $AQ_5$:

$$T_\alpha \geq T_{ACQ} \quad (1)$$

The "flat-top duration" $T_{GRO}$ (the duration of the middle region of a trapezoidal pulse in which the amplitude does not vary) of the readout gradient $GR_2$, $GR_3$ is in turn limited at the lower bound with these time periods $T_\alpha$ and $T_{ACQ}$ as follows:

$$T_{GRO} \geq T_{ACQ} + (2m-2)T_\alpha \quad (2)$$

The following therefore results for the time interval $T_\beta$ between two refocusing pulses $\beta_1$, $\beta_2$, $\beta_3$:

$$T_\beta \geq T_{GRO} + T_{REF} + 2 \cdot TG \quad (3)$$

$T_{REF}$ is thereby the duration of the refocusing pulses $\beta_1$, $\beta_2$, $\beta_3$, and TG is thereby the time that is respectively required for the gradient switchings that take place between the end of a refocusing pulse $\beta_1$, $\beta_2$, $\beta_3$ and the beginning of the flat-top of the successive readout gradients $GR_2$, $GR_3$, or between the end of the flat-top of a readout gradient $GR_2$, $GR_3$ and the beginning of the next refocusing pulse $\beta_1$, $\beta_2$, $\beta_3$. In a time interval TG, a spoiler gradient pulse $GS_3$, $GS_5$, $GS_6$, $GS_8$, $GS_9$, $GS_{11}$, a phase coding gradient $GP_1$, $GP_3$ or, respectively, a phase refocusing gradient $GP_2$, $GP_2$ is respectively switched, and the readout gradient $GR_2$, $GR_3$ is either ramped up or ramped down. Since these gradients are normally switched in parallel, the time period TG is determined by the longest of the cited gradient pulses or ramp times.

A gradient $GS_{2,1}$ in the slice-selection direction, whose 0th moment is equal to the negative of the sum of moment accumulated between the isodelay point in time of the first excitation pulse $\alpha_1$ and the end of the of the first slice-selection gradient $GS_{1,1}$ and the moment that is accumulated between the beginning of the second slice-selection gradient $GS_{1,2}$ and the isodelay point of the second excitation pulse $\alpha_2$, is switched between the slice-selection gradients $GS_{1,1}$, $GS_{1,2}$ of two successive slice excitation pulses $\alpha_1$, $\alpha_2$. Its algebraic sign is thus the reverse of the algebraic sign of the slice-selection gradients $GS_{1,1}$ and $GS_{1,2}$. The first half of this gradient $GS_{2,1}$ operates as a slice refocusing gradient of the first excitation pulse $\alpha_1$; the second half "predictively" compensates for exactly the moment that the spins excited by the first excitation pulse $\alpha_1$ accumulate as a result of the slice-selection gradient $GS_{1,2}$ of the second excitation pulse $\alpha_2$ and as a result of the slice refocusing gradient $GS_{2,2}$ of the second excitation pulse $\alpha_2$.

Given use of symmetrical slice-selection gradients $GS_{1,1}$, $GS_{1,2}$ and excitation pulses $\alpha_1$, $\alpha_2$, and the centering of the isodelay points in the middle of the flat top of the slice-selection gradients $GS_{1,1}$, $GS_{1,2}$ as shown in FIG. 3, the moment of this gradient $GS_{2,1}$ is thus $-2A$, and therefore equal to the negative moment $2A$ of a slice-selection gradients $GS_{1,1}$, $GS_{1,2}$. Under the cited assumptions, for a simpler understanding the action of the gradient can also be interpreted as follows: the gradient pulse $GS_{2,1}$ predictively compensates for the moment that the spins of the first slice—excited by the first excitation pulse $\alpha_1$—accumulate as a result of the slice-selection gradient $GS_{1,2}$ of the second excitation pulse $\alpha_2$. The gradient pulse $GS_{2,2}$ in the slice-selection direction immediately after the last excitation pulse $\alpha_2$ operates as a common slice refocusing pulse of the first excitation pulse $\alpha_1$ and the second excitation pulse $\alpha_2$.

An additional gradient pulse $GR_0$ is switched in the readout direction between two successive excitation pulses $\alpha_1$, $\alpha_2$, the moment C of which gradient pulse $GR_0$ coincides exactly with the moment that is accumulated between two successive echo signals $E_2$, $E_{1a}$, $E_{1b}$ in the readout direction; in FIG. 3:

$$C = T_\alpha \cdot A_{GR2} \quad (4)$$

wherein $A_{GR2}$ is the amplitude of a readout gradient $GR_2$, $GR_3$.

In contrast to this, the relative moment of the readout pre-phasing gradient $GR_1$ between the last excitation pulse $\alpha_2$ and the first refocusing pulse $\beta_1$ remains unchanged relative to the pulse sequence according to FIG. 1. Its moment is half as large as the moment of a readout gradient $GR_2$, $GR_3$ (i.e. $B+C$ in the example according to FIG. 2, or more generally $B+(m-1) \cdot C$ for m slices).

For graphical reasons, again only the formation of the first five echo signals $E_2$, $E_{1a}$, $E_{1b}$ of a sequence module is shown in FIG. 3. The sequence diagram of the complete sequence module with the complete echo train is obtained again via repetition of the framed sequence block SB. If the various echo signals should code various k-space lines, the moment of the phase coding gradient pulses $GP_1$, $GP_3$ and of the phase coding refocusing gradient pulses $GP_2$, $GP_3$ varies between the repetitions of the sequence block SB. All other gradients do not change their value in order to not infringe the aforementioned CPMG condition for the slice excited by the last excitation pulse $\alpha_2$ (more generally $\alpha_m$ given m slices).

Figure 4:
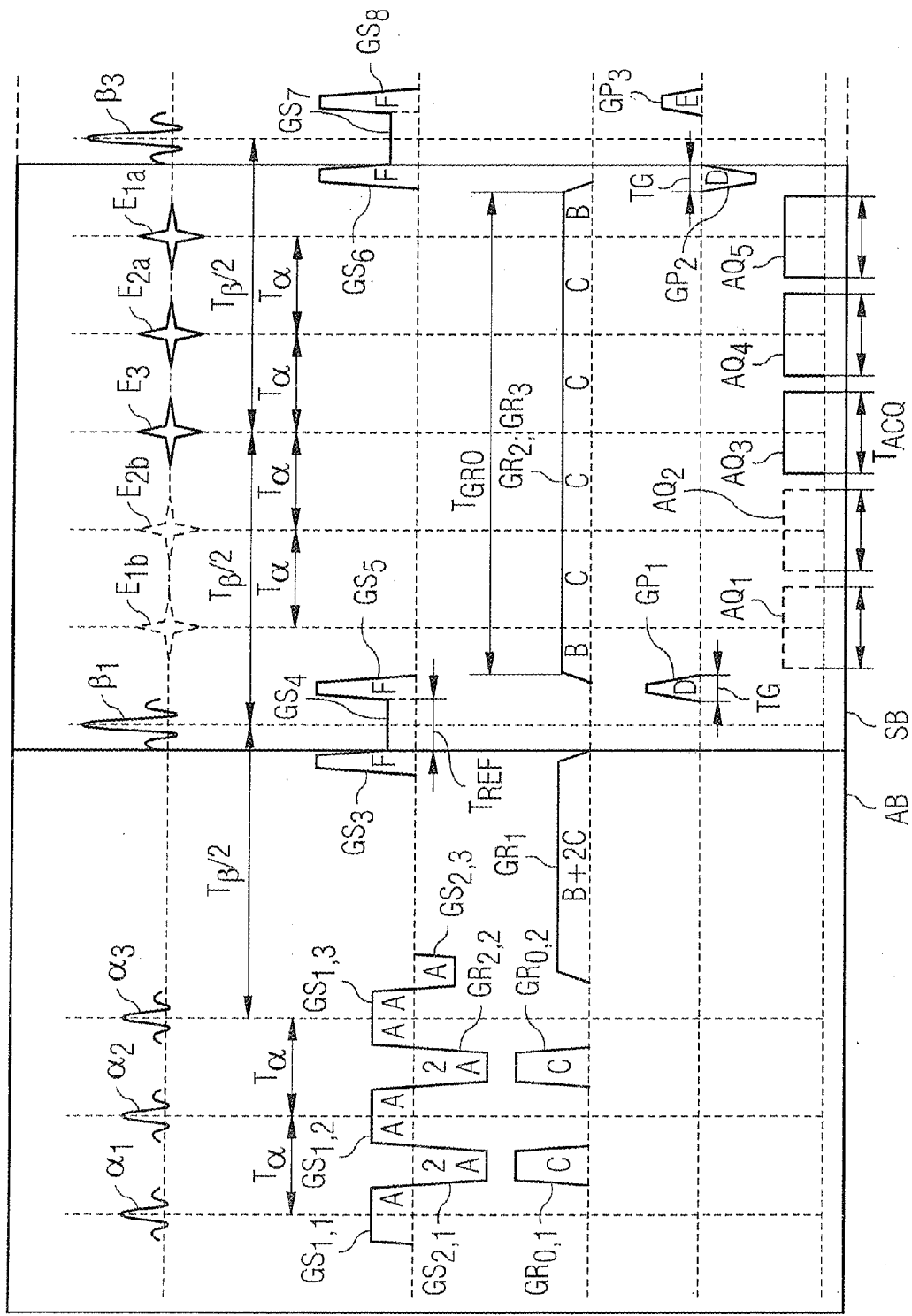
FIG. 4 shows a pulse scheme for a multislice TSE pulse sequence according to a second exemplary embodiment of the invention, with three simultaneously refocused slices.

FIG. 4 shows an additional embodiment of the pulse sequence according to the invention for simultaneous refocusing of three slices (i.e. with m=3). In contrast to FIG. 2, here three RF slice excitation pulses $\alpha_1$, $\alpha_2$, $\alpha_3$ (again respectively at a time interval $T_\alpha$ from one another) are therefore used with respective matching slice-selection gradients $GS_{1,1}$, $GS_{1,2}$, $GS_{1,3}$. Here as well, respective matching gradient pulses $GS_{2,1}$, $GS_{2,2}$ are switched in the slice-selection direction between the slice-selection gradients $GS_{1,1}$, $GS_{1,2}$, $GS_{1,3}$ of two successive slice excitation pulses $\alpha_1$, $\alpha_2$, $\alpha_3$.

In the case shown in FIG. 4 with symmetrical slice-selection gradients $GS_{1,1}$, $GS_{1,2}$, $GS_{1,3}$ and excitation pulses $\alpha_1$, $\alpha_2$, $\alpha_3$, as well as the centering of the isodelay points respectively in the middle of the flat-top of the slice-selection gradients slice-selection gradients $GS_{1,1}$, $GS_{1,2}$, $GS_{1,3}$, the effect of the gradient pulses $GS_{2,1}$, $GS_{2,2}$ can in turn be interpreted as follows: for the already excited spins, the gradient pulse $GS_{2,1}$, $GS_{2,2}$ respectively, predictively compensates the moment that these spins will accumulate as a result of the respective successive slice-selection gradients $GS_{1,2}$, $GS_{1,3}$. The gradient pulse $GS_{2,3}$ operates as a common slice refocusing gradient of all three slices. In the general case, it in turn applies that: the 0th moment of a gradient pulse $GS_{2,1}$, $GS_{2,2}$ is respectively equal to the negative sum of the moment that is accumulated between the isodelay point in time of the associated preceding excitation pulse and the end of this slice-selection gradient, and the moment that is accumulated between the beginning of the following slice-selection gradient and the isodelay point of the associated following excitation pulse.

Corresponding to the above explanations with regard to FIG. 3, here as well an additional gradient pulse $GR_{0,1}$, $GR_{0,2}$ is respectively switched in the readout direction between two successive excitation pulses $\alpha_1$, $\alpha_2$, $\alpha_3$.

Moreover, the width of the refocusing pulses $\beta_1$, $\beta_2$, $\beta_3$ is now expanded such that they respectively comprise the slices excited by all three excitation pulses $\alpha_1$, $\alpha_2$, $\alpha_3$. For example, this can again take place in that the bandwidth of the refocusing pulses $\beta_1$, $\beta_2$, $\beta_3$ remains unchanged relative to the sequence shown in FIG. 2, and the slice-selection gradient pulses $GS_4$, $GS_7$ is modified corresponding to the width and the slice interval of the individual slices.

For graphical reasons, only the formation of the excitation pulses $\alpha_1$, $\alpha_2$, $\alpha_3$ with the gradient pulses (and subsequently, directly following this the framed sequence block SB) is shown in FIG. 4, here with m=3 to 5 (namely 2·m−1) echo signals: $E_{1a}$, $E_{1b}$, $E2_a$, $E_{2b}$, $E_3$. By repeating the sequence block SB, the sequence diagram of the complete sequence module with the complete echo train is obtained again. Only as of the first repetition of the sequence block SB will the first two echo signals $E_{1b}$, $E_{2b}$ occur. Therefore, these are drawn with dashed lines in FIG. 4, just like the first two readout windows $AQ_1$, $AQ_2$ of the in total five readout windows $AQ_1$, $AQ_2$, $AQ_3$, $AQ_4$, $AQ_5$. The readout prephasing gradient $GR_1$, the readout gradient $GR_2$, the phase coding gradients $GP_1$, $GP_3$ and the phase refocusing gradient $GP_2$ are again designed analogous to the pulses according to FIG. 3. A more detailed description is therefore no longer necessary for this.

In the following, for better comprehension the functionality of the previously described pulse sequences according to the invention is explained in more detail, wherein these explanations generally apply to such pulse sequences with m excited and simultaneously refocused slices.

For this, the spins in the slice that are affected by the last excitation pulse $\alpha_m$ (for example the slice $S_2$ in FIG. 3 that is excited by the excitation pulse $\alpha_2$ and the slice $S_3$ in FIG. 4 that is excited by the excitation pulse $\alpha_3$) are initially considered. All earlier excitation pulses $\alpha_1, \ldots, \alpha_{m-1}$ (thus the first excitation pulse $\alpha_1$ in FIG. 3 and the first two excitation pulses $\alpha_1$ and $\alpha_2$ in FIG. 4) do not affect these spins since the resonance condition is not satisfied. As a result, all earlier gradient pulses also have no influence on these spins since the longitudinal magnetization is not affected by gradient fields. The pulse sequence for the spins of slice $S_m$ is therefore unaltered in principle relative to a conventional CPMG sequence as in FIG. 2.

A first spin echo is then generated at the point in time $T_\beta/2$ after the first refocusing pulse $\beta_1$, thus after the time period $T_\beta$ after the last slice excitation pulse $\alpha_m$, and can be read out as an echo signal $E_2$ (in FIG. 3), or as an echo signal $E_3$ (in FIG. 4) in the middle of the first readout gradient pulse $GR_2$.

The spins participating in this echo signal $E_2$ or, respectively, $E_3$ are refocused anew by the second refocusing pulse $\beta_2$ and form a second primary spin echo at the point in time $T_\beta/2$ after the second refocusing pulse $\beta_2$ (thus after the point in time $2 \cdot T_\beta$ after the excitation pulse $\alpha_m$). At this point in time, a first stimulated echo is also additionally formed by the common action of the last excitation pulse $\alpha_m$ and the first two refocusing pulses $\beta_1$ and $\beta_2$. The last excitation pulse $\alpha_m$ thereby flips the magnetization into the transversal plane, and upon materialization of the stimulated echo the first refocusing pulse $\beta_1$ operates as what is known as a restore pulse, meaning that it flips a portion of the transversal magnetization back into the longitudinal that then is flipped back again into the transversal plane by the second refocusing pulse $\beta_2$. It is said that this magnetization in the longitudinal direction is stored between the first refocusing pulse $\beta_1$ and second refocusing pulse $\beta_2$ since—as a longitudinal magnetization—it is not affected by the gradient fields and also is subject only to the relatively slow T1 relaxation time. Due to the fulfillment of the CPMG condition, the signals of the second primary spin echo and of the first stimulated echo superimpose constructively and can be read out as echo signal group $E_2$ (and $E_3$ in FIG. 4) in the middle of the second readout gradient ($GR_2$ in FIG. 3).

The number of different coherent echo paths increases in the later echoes of the echo signal group $E_2$ (or, respectively, $E_3$ in FIG. 4). Since the CPMG condition is satisfied, all coherent echo signals thereby form their echo signals simultaneously (respectively at the point in time $T_\beta/2$ after the preceding refocusing pulse $\beta_1$, $\beta_2$, $\beta_3$ in the middle of a readout gradient pulse $GR_2$, $GR_3$) and are in phase (meaning that the signals of the different echo paths superimpose constructively). Furthermore, the total moment of all gradient pulses that are switched in the readout direction and slice-selection direction at the point in time of the spin echoes of the echo signal group $E_2$ (and $E_3$ in FIG. 4) after the last slice excitation pulse $\alpha_m$ (thus slice excitation pulse $\alpha_2$ in FIG. 3 or slice excitation pulse $\alpha_3$ in FIG. 4) is zero.

In the following, the spins in a slice i that are excited by the excitation pulse $\alpha_i$ (with i=1, ..., m−1) that is not the last excitation pulse are generally considered (in the sequence according to FIG. 3 only two slices are excited, meaning that m=2, such that here only i=1 applies; in contrast to this, in the sequence according to FIG. 4 three slices are already excited, meaning that m=3, such that here the following statements apply for i=1 or 2). If earlier excitation pulses $\alpha_1, \ldots, \alpha_{i-1}$ exist, these do not affect the spins that are excited by the excitation pulse a; since the resonance condition is not satisfied. As a result, all earlier gradient pulses also have no influence on these spins since the longitudinal magnetization is not affected by the gradient fields.

Furthermore, the carrier frequency, the bandwidth of the subsequent slice excitation pulses $\alpha_{i+1}, \ldots, \alpha_m$ and the amplitude of the associated slice-selection gradient pulses $GS_{1,i+1}, \ldots, GS_{1,m}$ (i.e. the slice-selection gradient pulses $GS_{1,2}$ or, respectively, $GS_{1,3}$ in FIGS. 3 and 4) are selected so that the spins of the slice $\alpha_i$ are not affected by these later slice excitation pulses $\alpha_{i+1}, \ldots, \alpha_m$. However, since all gradient fields that are switched after an excitation pulse affect the spins that have been flipped in the transversal plane by this excitation pulse, the spins of the considered slice respectively accumulate (among other things) a 0th moment due to the slice-selection gradients $GS_{1,i+1}, \ldots, GS_{1,m}$ of all later slice excitation pulses $\alpha_{i+1}, \ldots, \alpha_m$. In order to avoid a dephasing of the signal of this slice due to the slice-selection gradients $GS_{1,2}$, $GS_{1,3}$ of the later excitation pulses $\alpha_{i+1}, \ldots, \alpha_m$, the aforementioned additional measure was taken of a negative gradient pulse $GS_{2,1}, \ldots, GS_{2,m-1}$ (i.e. specifically the negative gradient pulses $GS_{2,1}$ and $GS_{2,2}$ in FIGS. 3 and 4) that has the total moment −2A being radiated in the slice-selection direction between two successive slice excitation pulses $\alpha_1$ and $\alpha_2$, $\alpha_2$ and $\alpha_3$, ..., $\alpha_{m-1}$ and $\alpha_m$. One half of this moment −A of one of these negative gradient pulses $GS_{2,j}$ (j=1 ..., m−1) serves as a common slice refocusing moment for the slice-selection gradient $GS_{1,j}$ of the earlier excitation pulse $\alpha_j$—in FIG. 3, the description applies to the gradient $GS_{2,1}$ (j=1=1); in FIG. 4, the description applies to the gradient $GS_{2,1}$ (j=1) and $GS_{2,2}$ (j=2) insofar as the excitation pulse $\alpha_1$ (i=1) is considered, or the excitation pulse $\alpha_2$ (i=2) is considered for the gradient $GS_{2,2}$ (j=2). The other half of this moment −A serves as a pre-phasing gradient that compensates the positive moment that is accumulated by the slice-selection gradient $GS_{1,j+1}$ of the later excitation pulse $\alpha_{j+1}$ between the beginning of the slice-selection gradient $GS_{1,j}$ and isodelay point of the later excitation pulse $\alpha_{j+1}$. Since a gradient field has no effect on spins that are aligned longitudinally relative to the basic field, the negative gradient pulse $GS_{2,1}$ between the slice excitation pulses $\alpha_1$ and $\alpha_{i+1}$ has no influence on the spins that are excited by all later excitation pulses $\alpha_{l+1}, \ldots, \alpha_m$.

After the last slice excitation pulse $\alpha_m$ or, respectively, the last slice-selection gradient pulse $GS_{1,m}$, a negative gradient pulse $GS_{2,m}$ in the slice-selection direction is accordingly further radiated, which now has only one half $-A$ of the moment of the other negative gradient pulses $GS_{2,1}, GS_{2,m-1}$ in the slice-selection direction, since this must still serve only as a "slice refocusing gradient" of the last slice.

Due to the expansion of the pulses that is explained above, the first refocusing pulse $\beta_1$ simultaneously refocuses the signal of all spins that were excited by one of the m excitation pulses $\alpha_1, \ldots, \alpha_m$. The spins of the first slice that were excited by the excitation pulse $\alpha_1$ are thus refocused at the point in time $(m-1)\cdot T_\alpha + T_\beta/2$ after the first refocusing pulse $\beta_1$ (thus $2\cdot(m-1)\cdot T_\alpha + T_\beta$ after the excitation pulse $\alpha_1$) at a first spin echo.

In that the gradient $GR_2$ in the readout direction has a moment C between two successive echo signals, together with the common readout pre-phasing gradient pulse $GR_1$ with a moment $B+C$ between the last excitation pulse $\alpha_m$ and first refocusing pulse $\beta_1$ it is ensured that the total moment in the readout direction is equal to zero for the spins of the first slice at the point in time of the first spin echoes. The gradient echo and the RF spin echo of the spins of the first slice thus arise simultaneously and can be read out as an echo group $E_{1a}$ at the point in time $(m-1)\cdot T_\alpha + T_\beta/2$ after the first refocusing pulse $\beta_1$.

It is noted that the spins of the previously considered slice m (the second slice in FIG. 3 or, respectively, the third slice in FIG. 4) at the point in time of the first spin echo of the slice 1 have already accumulated the moment $(m-1)\cdot C$ (thus the moment C in FIG. 3 and the moment 2C in FIG. 4) and are thus dephased. The basis lies in that the spins of the slice m have not "seen" the gradients $GR_{0,1}, GR_{0,2}$ in the readout direction between the excitation pulses since the gradients were switched chronologically before the excitation of the spins. Conversely, the gradients $GR_{0,1}, GR_{0,2}$ act on the spins of the first slice so that these are still dephased by a moment $(m-1)\cdot C$ at the point in time $T_\beta/2$ of the spin echo of the m-th slice, and thus supply no signal contribution to the m-th echo group (thus to echo group $E_2$ in FIG. 3 or $E_3$ in FIG. 4). The measure of the intermediate switching of the gradient pulses $GR_{0,1}, GR_{0,2}$ in the readout direction that is described above, together with the chronological arrangement of the slice excitation pulses $\alpha_2, \ldots, \alpha_m$ and slice refocusing pulses $\beta_1, \beta_2, \beta_3, \ldots$ thus serves to separate the readout window $AQ_1, \ldots, AQ_{2m-1}$ of different slices.

The signal of the first spin echo of the slice is then refocused again by the second refocusing pulse $\beta_2$ and forms a second primary spin echo at the point in time $T_\beta/2-(m-1)\cdot T_\alpha$ after the second refocusing pulse $\beta_2$—thus $(m-1)\cdot T_\alpha + T_\beta/2 + T_\beta + T_\beta/2 - (m-1)\cdot T_\alpha = 2\cdot T_\beta$ after the excitation pulse $\alpha_1$. At this point in time, the moment B accumulated by the first readout gradient $GR_2$ after the first spin echo of the first slice is also compensated exactly by the second readout gradient pulse $GR_3$ so that the echo can be read out in the echo group $E_{1b}$. The signal of the other slices at this point in time is again further dephased by the readout gradient pulse $GR_2$ (for example of the first spin echoes of the second slice in the case of m=2), or by the readout pre-phasing gradient pulse $GR_1$ (for example in the case of m=2 of the first stimulated echo of the second slice S2) (respectively by the moment C for m=2).

However, the first stimulated echo of the first slice is generated at the point in time $T_\beta/2+(m-1)\cdot T_\alpha$ after the second refocusing pulse $\beta_2$, thus $(m-1)\cdot T_\alpha + T_\beta/2 + T_\beta + T_\beta/2 + (m-1)\cdot T_\alpha = 2\cdot(m-1)\cdot T_\alpha + 2\cdot T_\beta$ after the excitation pulse $\alpha_1$. The spins of the first slice that contribute to this stimulated echo have been located in the transversal plane between the first excitation pulse $\alpha_1$ and the first refocusing pulse $\beta_1$ and thereby accumulate the moment $B+m\cdot C$ in the readout direction. In contrast to this, their signal was stored in the longitudinal direction between the two first refocusing pulses $\beta_1$ and $\beta_2$, and the first readout gradient thus has no effect on them. They were then flipped back into the transversal plane by the second refocusing pulse $\beta_2$. As a result of the readout gradient pulse $GR_3$, they thus again accumulate a moment $B+m\cdot C$ between second refocusing pulse $\beta_2$ and the point in time of the stimulated echo, which moment $B+m\cdot C$ exactly compensates the accumulated moment before the first refocusing pulse $\beta_1$. The first stimulated echo can thus be read out as an echo group $E_{1a}$. At this point in time, the spin echo of the first slice that is read out in the echo group $E_{1b}$ is already dephased by a moment $2m\cdot C$ (thus 2C in the sequence according to FIGS. 3 and 6C according to FIG. 4), and the signal of the last slice m that is read out in the echo signal group $E_m$ is dephased by a moment $(m-1)\cdot C$.

The measure of inter-switching the gradient pulses $GR_{0,1}, GR_{0,2}$ in the readout direction thus serves not only for additional separation of echoes of different slices, but also for separation of different coherent echo paths of the same slice. A destructive interference of the signals of different coherent echo paths of the same slice is avoided via this separation since all remaining slices (except for the last excited slice m) do not satisfy the CPMG condition.

The time interval between two successive refocusing pulses is designated as an echo spacing $T_\beta$. The number of the echo spacings $T_\beta$ in which the spins that follow this echo path have been located in the transversal plane is characteristic of a coherent echo path. For the first spin echo of the first slice in the echo group $E_{1a}$, this time is $2\cdot(m-1)\cdot T_\alpha + 1\cdot T_\beta$; this time interval is composed of the time interval $(m-1)\cdot T_\alpha + T_\beta/2$ between excitation pulse $\alpha_1$ and first refocusing pulse $\beta_1$, as well as the time interval $T_\beta/2+(m-1)\cdot T\alpha$ after the first refocusing pulse $\beta_1$. For the first stimulated echo (likewise acquired in the first echo group $E_{1a}$), this time is also $2\cdot(m-1)\cdot T_\alpha + 1\cdot T_\beta$ (again $(m-1)\cdot T_\alpha + T_\beta/2$ between excitation pulse $\alpha_1$ and first refocusing pulse $\beta_1$ and $T_\beta/2+(m-1)\cdot T_\alpha$ after the second refocusing pulse $\beta_2$); for the directly refocused first spin echo that is read out after the second refocusing pulse $\beta_2$ in the echo group $E_{1b}$, this time is $2\cdot T_\beta$ (time interval $(m-1)\cdot T_\alpha + T_\beta/2$ between first excitation pulse $\alpha_1$ and first refocusing pulse $\beta_1$, time interval $T_\beta$ between first and second refocusing pulse, and time interval $T_\beta/2-(m-1)\cdot T_\alpha$ after the second refocusing pulse $\beta_2$).

In general, it applies that coherent echo paths in which the spins that follow this echo path have been located in the transversal plane for a time period $2\cdot(m-1)\cdot T_\alpha + u\cdot T_\beta$ (wherein u is an odd whole number) are acquired in the echo group $E_{1a}$ (thus in the respective third readout window after a refocusing pulse $\beta_2, \beta_3, \ldots$ in the example of FIG. 3), and echo paths in which the corresponding time period amounts to $g\cdot T_\beta$ (wherein g is an even whole number) are acquired in the echo group $E_{1b}$ (thus in the respective first readout window after a refocusing pulse $\beta_2$, $\beta_3$, . . . in the example of FIG. 3). The signals of the various echo paths of a group add up coherently (due to the spin echo principle) and therefore do not need to be split up into different readout windows.

Figure 5:
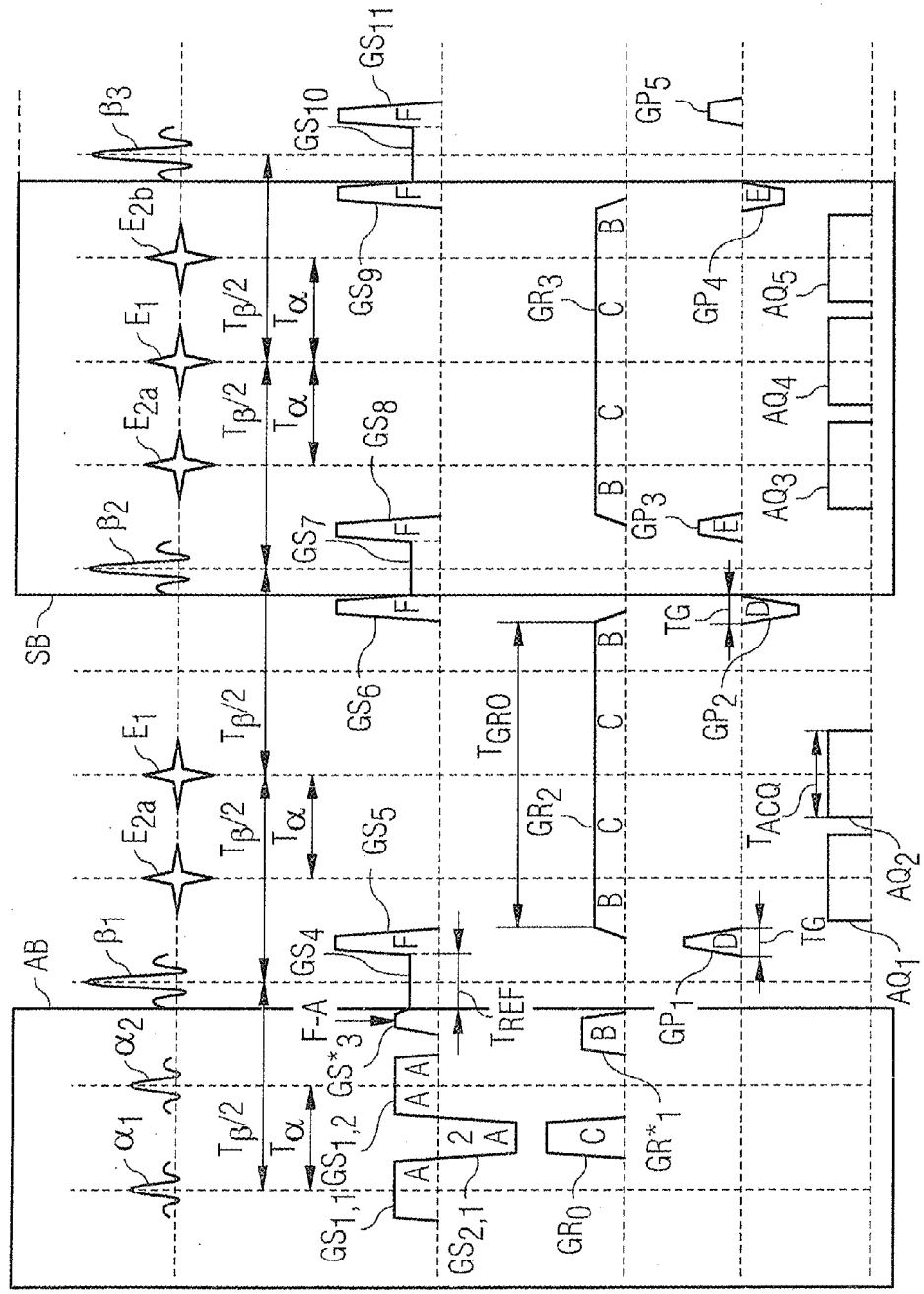
FIG. 5 shows a pulse scheme for a multislice TSE pulse sequence according to a third exemplary embodiment of the invention, with two simultaneously refocused slices.

FIG. 5 shows an additional embodiment of the pulse sequence according to the invention for simultaneous refocusing of two slices (i.e. with m=2).

In contrast to FIGS. 3 and 4, here the CPMG condition is satisfied for the first slice excited with the RF excitation pulse $\alpha_1$. The time interval $T_\alpha/2$ between the first RF excitation pulse $\alpha_1$ and the first common refocusing pulse $\beta_1$ is therefore accordingly twice as long as the time interval $T_\beta$ between two successive refocusing pulses $\beta_1$, $\beta_2$, $\beta_3$.

If it is allowed that the later radiated RF excitation pulses ($\alpha_2$ in FIG. 5) do not influence the spins of the first slice due to the non-fulfillment of the resonance condition, the fulfillment of the CPMG can most simply be detected via the comparison with FIG. 2. The gradient pulse $GS_{2,1}$ predictively compensates the slice-selection gradient $GS_{1,2}$ of the second slice affected by the second RF excitation pulse $\alpha_2$. From the point of view of static spins of the first slice, both gradients can thus be considered to be nonexistent. The common slice refocusing gradient of the two slices with the moment −A is combined in FIG. 5 with the left spoiler gradient $GS_5$ of the first refocusing pulse $\beta_1$ (with moment F) to form the gradient $GS_3^*$ with a moment F−A. A combination of gradient pulses means the merging of multiple gradient pulses into a single gradient pulse such that the effective 0th gradient moment (thus the area) is retained. The gradients $GS_2'$ and $GS_3'$ in the sequence according to FIG. 2 could have been combined accordingly.

From the point of view of the spins of the first slice, the two gradients $GR_0$ with moment C and $GR_1^*$ with moment B can be considered to be combined in the readout direction into a single gradient pulse with moment B+C. This "effective readout pre-phasing gradient" corresponds to the gradient GR1' of the sequence according to FIG. 2 whose moment is half as large as the moment of the readout gradient $GR_2$, $GR_1$. From the viewpoint of the spins of the second slice affected by the RF excitation pulse $\alpha_2$, however, the separation of the two gradients $GR_0$ and $GR_1^*$ is advantageous since these spins do not see the gradient $GR_0$ as a longitudinal magnetization.

The time interval between successive RF excitation pulses $\alpha_1$, $\alpha_2$ is in turn $T_\alpha$; the interval between the second excitation pulse $\alpha_2$ and the first refocusing pulse $\beta_1$ is thus $T_\beta/2-T_\alpha$. A first spin echo thus forms in the time interval $T_\beta/2-T_\alpha$ after the first refocusing pulse $\beta_1$, and a first stimulated echo forms $T_\beta/2-T_\alpha$ after the second refocusing pulse $\beta_2$. Since the gradient moment (acquired in the readout direction and slice-selection direction) of the spins of the second slice that follow the respective echo paths is zero, the signal of this echo can respectively be read out in the echo signal group $E_{2a}$. The chronological arrangement of the RF pulses thus in turn ensures that these echoes of the second slice are separated from the echoes of the first slice by a time interval $T_\alpha$.

The first spin echo that is directly refocused by the second refocusing pulse $\beta_2$ forms $T_\alpha+T_\beta/2$ after the second refocusing pulse $\beta_2$ in the echo signal group $E_{2b}$, and therefore is separated in time by $T_\alpha$ from the echoes of the first slice and by $2T_\alpha$ from the first stimulated echo. This separation of different of different echo paths of the second slice whose transversal times do not differ by even-number multiples of $T_\beta$ is again advantageous, since the sequence does not satisfy the CPMG condition from the point of view of the spins of the second slice.

The expansion to more than two simultaneously refocused slices is possible, analogous to the procedure from the sequence from FIG. 3 to the sequence from FIG. 4:

add additional RF pulses (with slice-selection gradient) at the interval $T_\alpha$ from the respective last RF excitation pulse, switch a gradient pulse with moment −2A in the slice selection direction and a gradient pulse with moment C in the readout direction between two respective, successive RF excitation pulses, and analogous adaptation of the sequence block SB for the up to 2m−1 echoes and readout intervals.

If all k-space lines of one of the excited slices that are necessary for image reconstruction are coded with one sequence module (i.e. a one-time excitation of each of the m slices and the subsequent echo train) or multiple sequence modules (i.e. with repeated excitation of the m slices, each followed by a subsequent echo train) of a pulse sequence according to FIG. 3, 4 or 5, a complete raw data set is obtained for each of the 2m−1 echo groups. Precisely one data set is thereby obtained for the featured slice acquired in CPMG mode (i.e. the last excited slice given use of the sequence from FIG. 3 or FIG. 4 or the first excited slice given use of the sequence from FIG. 5). The image or the images of this featured slice can then be reconstructed conventionally (thus in a manner as if the data had been acquired with a conventional pulse sequence as shown in FIG. 2) from the data of the respective echo signal group ($E_2$ given use of the sequence from FIG. 3, $E_3$ given use of the sequence from FIG. 4, $E_1$ given use of the sequence from FIG. 5).

In contrast to this, two complete raw data sets are respectively obtained for the remaining slices via the division into different echo signal groups. Different possible processings of these raw data sets are explained in the following in the example of the echo signal groups $E_{1a}$, $E_{1b}$ of the first slice from FIG. 3 or FIG. 4.

If only magnitude images are required, in a first embodiment a magnitude image can respectively be reconstructed from the raw data set of the echo signal group $E_{1a}$ and the raw data set of the echo signal groups $E_{1b}$ (for example insofar as acquired k-space points lie on the grid points of a Cartesian grid in the typical manner, via a two-dimensional Fourier transformation from k-space populated with these raw data into image space), and subsequently add the two magnitude images to improve the signal-to-noise ratio. Due to the preceding magnitude calculation, the incoherent phase information of the two data sets leads to no signal cancellation. This procedure is analogous to a procedure as it is described in the article "SPLICE: Sub-second diffusion-sensitive MR imaging using a modified fast spin-echo acquisition mode" by Fritz Schick, appearing in the journal Magnetic Resonance in Medicine, Volume 38, Issue 4, Pages 638-644, October 1997. There a TSE sequence is described in which the CPMG condition is not satisfied and the slices are refocused separately.

An image with an improved signal-to-noise ratio can be acquired with an alternative method that resorts to the of sum-of-squares method. The combined image $M_1(x,y)$ of the first slice—i.e. the image point (pixel) values $M_1(x,y)$ of the first image—is calculated as follows:

$$M_1(x,y) = \sqrt{|I_{1a}(x,y)|^2 + |I_{1b}(x,y)|^2} \tag{5}$$

wherein $I_{1a}(x,y)$ is the complex image point of the image reconstructed from the raw data set of the echo signal group $E_{1a}$ with the spatial image coordinates (x,y) and $I_{1b}(x,y)$ of the corresponding complex image point of the image reconstructed from the raw data set of the echo group $E_{1b}$. $|I_{1a}(x,y)|$ designates the absolute value of the complex image point:

$$|I_{1a}(x,y)|=\sqrt{Re\{I_{1a}(x,y)\}^2+Im\{I_{1a}(x,y)\}^2} \quad (6)$$

and $|I_{1b}(x,y)|$ correspondingly designates the absolute value of the complex image point $I_{1b}(x,y)$:

$$|I_{1b}(x,y)|=\sqrt{Re\{I_{1b}(x,y)\}^2+Im\{I_{1b}(x,y)\}^2} \quad (7)$$

In a further preferred embodiment, the complex two images $I_{1a}(x,y)$ and $I_{1b}(x,y)$ are initially subjected to a phase correction $$\tilde{I}_{1a}(x,y)=I_{1a}(x,y)e^{-i\hat{\phi}_{1a}(x,y)} \quad (8)$$

$$\tilde{I}_{1b}(x,y)=I_{1b}(x,y)e^{-i\hat{\phi}_{1b}(x,y)} \quad (9)$$

The exponents $\hat{\phi}_{1a}(x,y)$ and $\hat{\phi}_{1b}(x,y)$ are what are known as "phase correction maps" ("phase maps") that can be calculated from the acquire data, as is explained later using FIG. 6. The phase-corrected images $\tilde{I}_{1a}(x,y)$, $\tilde{I}_{1b}(x,y)$ are subsequently added up later in complex number space into a complex, combined image for the appertaining slice according to $$\tilde{I}_1(x,y)=\tilde{I}_{1a}(x,y)+\tilde{I}_{1b}(x,y) \quad (10)$$

From this combined image, a magnitude image can then be generated according to $$\tilde{M}_1(x,y)=\sqrt{Re\{\tilde{I}_1(x,y)\}^2+Im\{\tilde{I}_1(x,y)\}^2} \quad (11)$$

real part images can be generated according to $$\tilde{R}_1(x,y)=Re\{\tilde{I}_1(x,y)\} \quad (12)$$

real part magnitude images can be generated according to $$\tilde{R}_{B1}(x,y)=|Re\{\tilde{I}_1(x,y)\}| \quad (13)$$

or phase images can be generated according to $$\tilde{\varphi}_1(x,y) \sim \operatorname{atan}\left(\frac{Im\{\tilde{I}_1(x,y)\}}{Re\{\tilde{I}_1(x,y)\}}\right). \quad (14)$$

Figure 6:
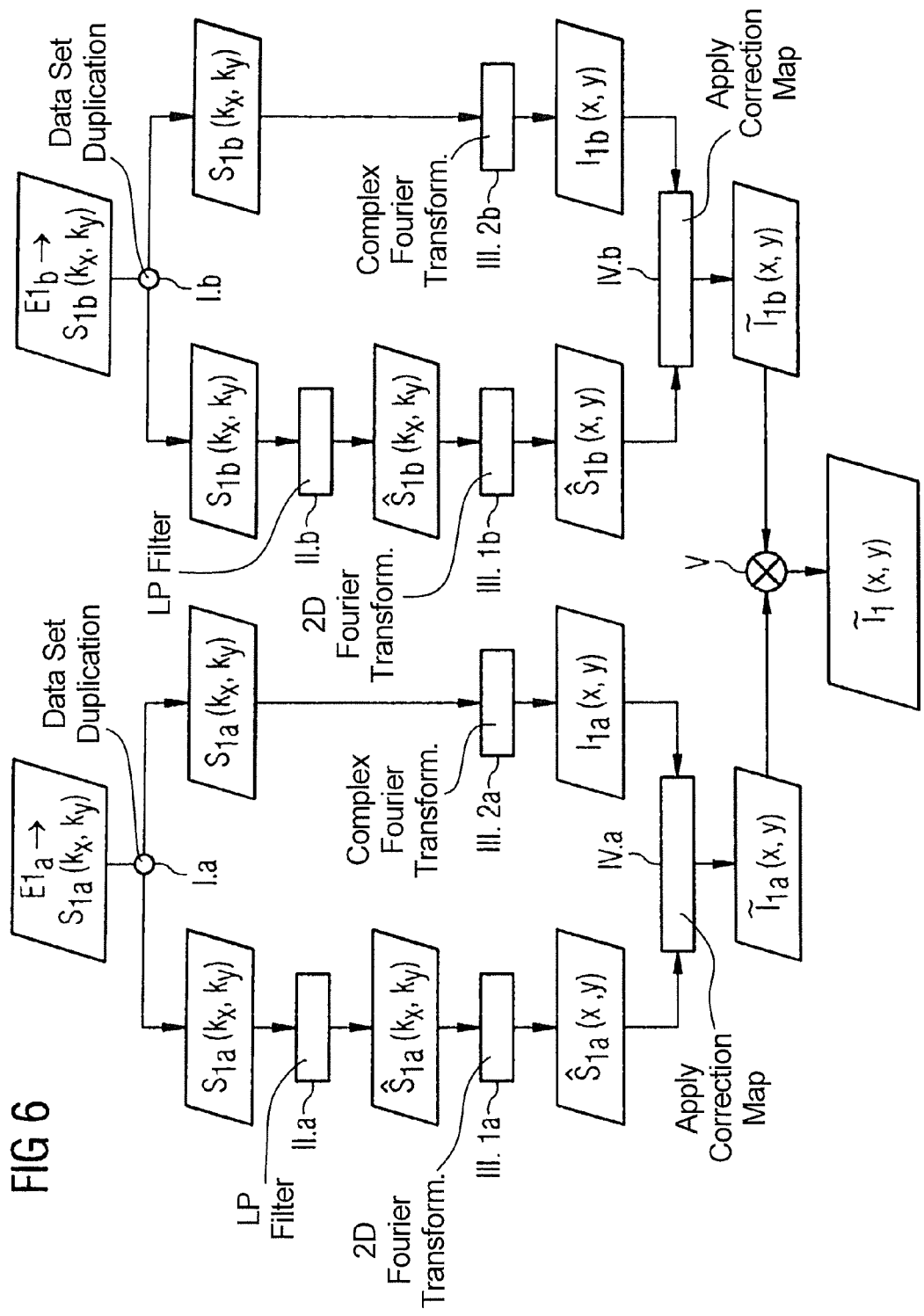
FIG. 6 is a flowchart for a possible workflow of a method for complex combination of the raw data acquired in different readout windows.

A flowchart of how the phase correction maps $\hat{\phi}_{1a}(x,y)$ and $\hat{\phi}_{1b}(x,y)$ that are necessary in Equations (8) and (9) (for example) can be calculated from the acquired data is shown in FIG. 6.

For this purpose, the raw data set $S_{1a}(k_x,k_y)$ of the first echo group is initially duplicated in Step I.a, and the raw data set $S_{1b}(k_x,k_y)$ of the second echo group is initially duplicated in Step I.b.

As in a conventional standard reconstruction, in Step III.2*a* and III.2*b* a complex image $I_{1a}(x,y)$ and $I_{1b}(x,y)$ is respectively obtained from the one duplicate with the use of a two-dimensional, complex Fourier transformation.

The other duplicate is respectively filtered in Steps II.a and II.b with a low-pass filter. The filtered raw data sets $\hat{S}_{1a}(k_x, k_y)$ of the first echo group and $\hat{S}_{1b}(k_x, k_y)$ of the second echo group are subsequently transformed with a two-dimensional (2D) Fourier transformation in image space in Step III.1a and III.1b in order to obtain spatially low-resolution images $\hat{I}_{1a}(x,y)$ and $\hat{I}_{1b}(x,y)$.

The sought phase correction maps $\hat{\phi}_{1a}(x,y)$ and $\hat{\phi}_{1b}(x,y)$ could now be calculated direction via a phase extraction from the spatially low-resolution images according to $$\hat{I}_{1a}(x,y)=|\hat{I}_{1a}(x,y)|e^{i\hat{\phi}_{1a}(x,y)} \quad (15)$$

and $$\hat{I}_{1b}(x,y)=|\hat{I}_{1b}(x,y)|e^{i\hat{\phi}_{1b}(x,y)}. \quad (16)$$

However, in terms of computation it is normally more advantageous to complexly conjugate each image point of the spatially low-resolution images $\hat{I}_{1a}(x,y)$ or, respectively, $\hat{I}_{1b}(x,y)$ and to divide each image point by its absolute value. In step IVa and IVb, the correction maps that are thus obtained are then multiplied per) (x,y pixel with the spatially high resolution images $I_{1a}(x,y)$ or, respectively, $I_{1b}(x,y)$, and thus the phase-corrected images $$\tilde{I}_{1a}(x, y) = I_{1a}(x, y) \frac{\hat{I}^*_{1a}(x, y)}{|\hat{I}_{1a}(x, y)|} \quad (17)$$

and $$\tilde{I}_{1b}(x, y) = I_{1b}(x, y) \frac{\hat{I}^*_{1b}(x, y)}{|\hat{I}_{1b}(x, y)|} \quad (18)$$

are arrived at directly from Equations (8) and (9). A complex addition according to Equation (10) in order to arrive at the combined image $\tilde{I}_1(x,y)$ of the appertaining slice can then take place in Step V.

Additional preferred embodiments are discussed in the following.

A short echo spacing ($T_\beta$ in the figures) normally positively affects the image quality in turbo spin echo imaging. In the method according to the invention, the number of readout windows per refocusing pulse with 2m−1 is increased relative to a classical single slice turbo spin echo sequence which has only one readout window per refocusing pulse (as shown in FIG. 2). Nevertheless, in order to realize a short echo spacing, the pulse sequence according to the invention is preferably used with a large readout gradient in order to traverse k-space to be acquired in an optimally short amount of time in the readout direction. However, the maximum gradient amplitude $A_{max}$ is technically limited by the gradient system of the magnetic resonance installation. As is explained above using Equation (4), in the pulse sequence according to the invention the same gradient moment $C=T_\alpha \cdot A_{GRO}$ in the readout direction as between two successive echo signals is also to be switched in the time period $T_\alpha$ between two successive slice excitation pulses $\alpha_1$, $\alpha_2$, $\alpha_3$. However, the time provided for this is shorter by the duration of a slice excitation pulse $\alpha_1$, $\alpha_2$, $\alpha_3$ than the duration $T_\alpha$. The maximum readout gradient is thus always smaller than the maximum amplitude $A_{max}$ of the gradient system, and can be chosen to be closer to the maximum amplitude $A_{max}$ the shorter that the duration of an excitation pulse $\alpha_1$, $\alpha_2$, $\alpha_3$ is chosen. In a preferred embodiment, the duration of a slice excitation pulse $\alpha_1$, $\alpha_2$, $\alpha_3$ is therefore selected to be as short as possible under consideration of the maximum $B_1$ amplitude that can be realized by the radio-frequency transmission system of the magnetic resonance tomography system and under consideration of SAR limits. Since the flip angle to be realized by an excitation pulse $\alpha_1$, $\alpha_2$, $\alpha_3$ is normally smaller by 90° than the flip angle of a refocusing pulse $\beta_1$, $\beta_2$, $\beta_3$, at a given maximum $B_1$ amplitude of the radio-frequency transmission system, it is normally possible in particular to select the duration of an excitation pulse $\alpha_1$, $\alpha_2$, $\alpha_3$ to be shorter than the duration of a refocusing pulse $\beta_1$, $\beta_2$, $\beta_3$.

In the pulse sequence according to the invention, as explained above the raw data for precisely one featured slice of the m slices in total are respectively acquired per sequence module or, respectively, echo train in CPMG mode (i.e. while satisfying the aforementioned CPMG condition), and the signals of all coherent echo paths are read out simultaneously, while the signals are read out separately in two respective readout windows for the remaining m−1 slices and are only combined later in the image reconstruction. This featured slice is the last excited slice in the pulse sequences shown in FIGS. 3 and 4 and the first excited slice in the pulse sequence according to FIG. 5. For example, in a single-shot variant of the pulse sequence according to the invention in which a complete raw data set of the m slices is respectively acquired with a single echo train, this leads to the situation that the images of the featured slice normally have a higher signal-to-noise ratio than the images of the m−1 other slices.

In a further, preferred embodiment, the invention can be realized in a multi-shot variant of the sequence according to the invention in order to avoid acquisition-dependent differences between adjacent slices that, for example, could hinder a tracking of a lesion in a direction orthogonal to the image plane during the finding by a radiologist. Multi-shot here means that the raw data required for image reconstruction are acquired with multiple sequence modules, thus that multiple echo trains are formed. In the preferred multi-shot variant, such signal differences are avoided or, respectively, severely reduced in that the featured slice is permuted from echo train to echo train such that at least approximately an m-th of the raw data of each of the m slices is acquired in the CPMG mode, which has the strongest signal. It is important that the data acquired in various modes are sorted in k-space and computationally manipulated before a sorting in k-space, such that artifacts as a result of the cited signal differences are avoided.

In the following, the avoidance or, respectively, reduction of the acquisition-dependent signal differences is explained in detail in the example of a PROPELLER variant (PROPELLER=Periodically Rotated Overlapping Parallel Lines with Enhanced Reconstruction) of the sequence according to the invention. PROPELLER is a turbo spin echo sequence—known from the journal article "Motion Correction With PROPELLER MRI: Application to Head Motion and Free-Breathing Cardiac Imaging" by James Pipe, appearing in the journal Magnetic Resonance in Medicine 42:963-969 (1999)—that acquires a Cartesian k-space segment of a slice with each echo train, which k-space segment includes the k-space center. In PROPELLER imaging, the entirety of k-space of the slice is acquired with multiple echo trains, wherein the Cartesian k-space segments acquired by different echo trains are rotated counter to one another around the k-space center.

With each echo train for each of the m simultaneously refocused slices, a PROPELLER variant of the pulse sequence according to the invention acquires one (featured slice) or, respectively, two (remaining m−1 slices) Cartesian k-space segments that respectively include the k-space center. The k-space segments acquired in different echo trains are respectively rotated counter to one another around the k-space center.

Figure 7:
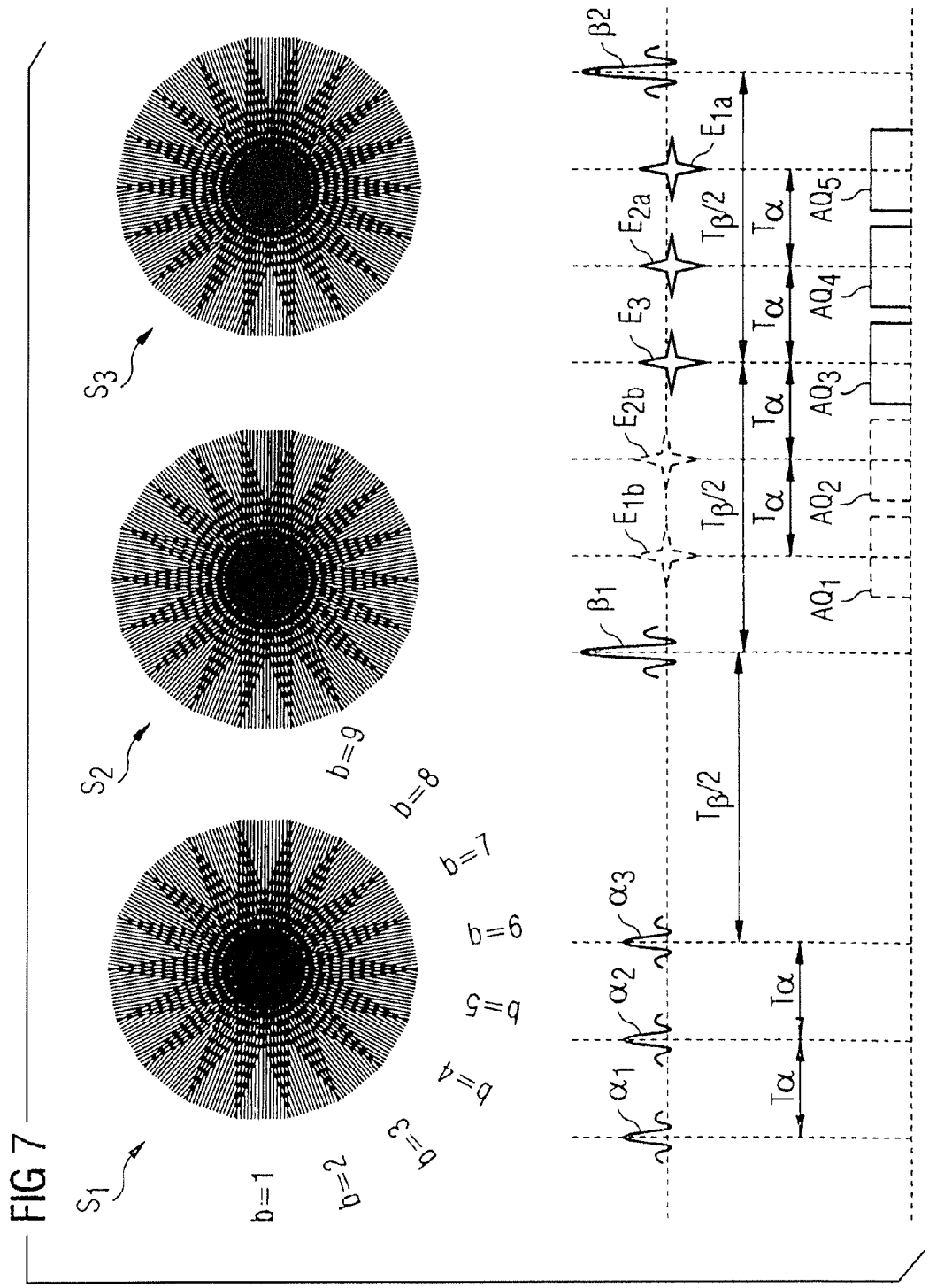
FIG. 7 shows a pulse scheme for a variant of a multislice TSE pulse sequence according to the second exemplary embodiment of the invention, specifically for a PROPELLER TSE sequence, and moreover a representation of the k-space trajectories through k-spaces for three slices.

FIG. 7 shows as an example how circular k-space can be acquired by m=3 adjacent slices with a PROPELLER variant of a sequence according to FIG. 4. For this purpose, k-space of the three slices $S_1$, $S_2$, $S_3$ is respectively shown in the upper part of the Figure; under this are again the slice excitation pulses $\alpha_1$, $\alpha_2$, $\alpha_3$ and refocusing pulses $\beta_1$, $\beta_2$, . . . and the readout windows $AQ_1$, $AQ_2$, $AQ_3$, $AQ_4$, $AQ_5$ of the pulse diagram from FIG. 4. The sequence from FIG. 4 is executed nine times in total to cover three circular k-spaces. If all k-space lines of a segment should be measured, the echo train length (i.e. the number of refocusing pulses $\beta_1$, $\beta_2$, . . . ) is then chosen to be at least as large as the number of k-space lines per propeller blade. The indexing or numbering of k-space segments b=1, . . . , 9 (which are also designated as "propeller blades") takes place in the rotation direction of the rotation angle.

In order to avoid a different signal-to-noise ratio of the images reconstructed from the measured raw data, in the PROPELLER variant each m-th k-space segment can be acquired in each slice in the CPMG mode. For this, the direction of the readout gradient and the phase coding gradient is rotated between the individual repetitions corresponding to the alignment of the respectively acquired k-space segment. The k-space segments of a slice that are acquired with different echo trains are thus rotated around the k-space center relative to one another. In the example according to FIG. 7, for example, the propeller blades with index b=1, b=4 and b=7 are acquired with the first three echo trains, and the slice $S_1$ is thereby respectively excited with the excitation pulse $\alpha_1$; the slice $S_2$ is excited with the excitation pulse $\alpha_2$; and the slice $S_3$ is excited with the excitation pulse $\alpha_3$. For example, the propeller blades with index b=2, b=5 and b=8 are acquired with the next three echo trains. In this last revolution, the first excitation pulse $\alpha_1$ respectively excites the slice $S_2$, the second excitation pulse $\alpha_2$ respectively excites the slice $S_3$ and the third excitation pulse $\alpha_3$ respectively excites the slice $S_1$.

Figure 8:
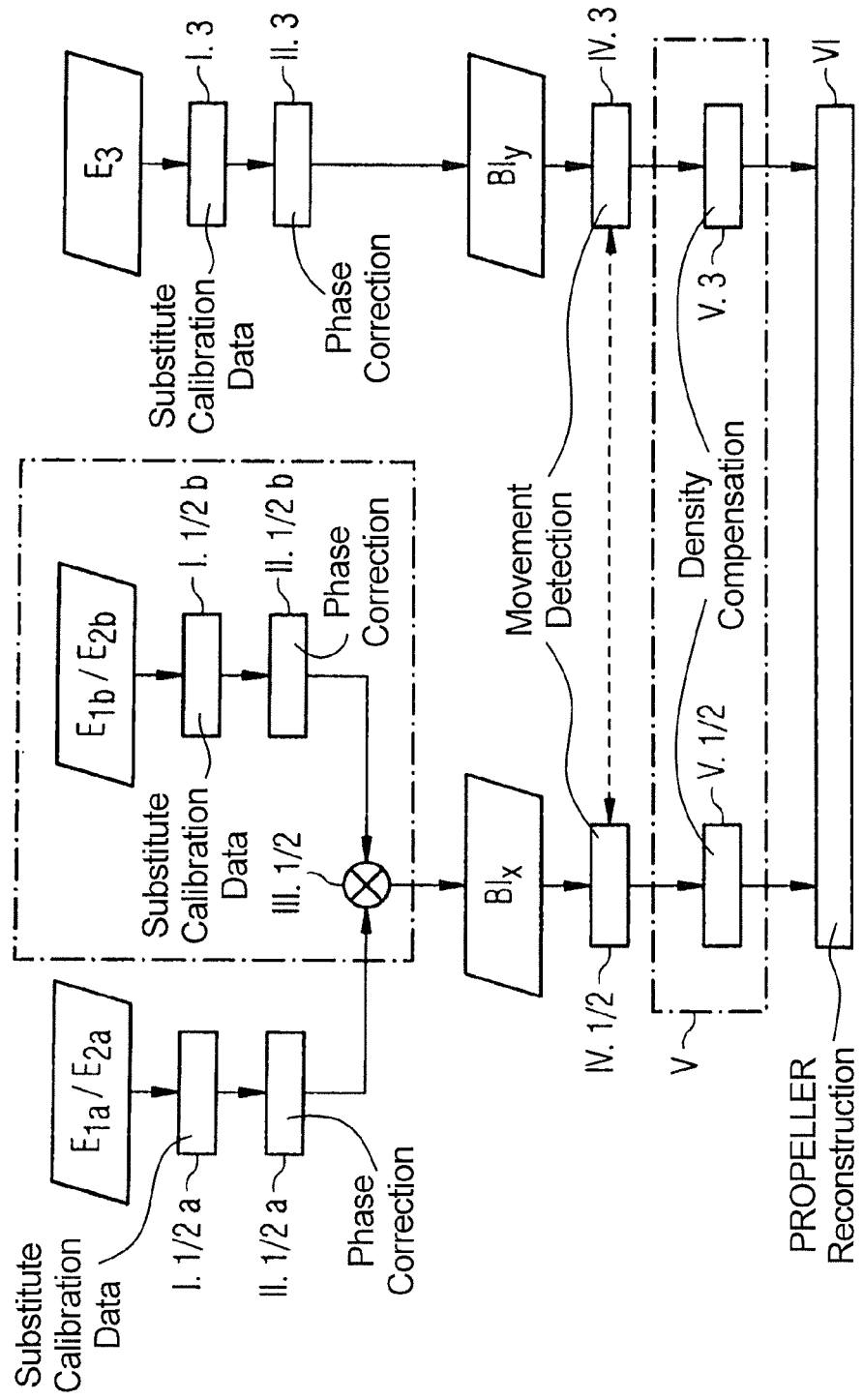
FIG. 8 a flowchart for an embodiment of a method for combination of the raw data acquired in different readout windows from a PROPELLER TSE sequence with a pulse scheme according to FIG. 7.

A flowchart for a possible PROPELLER reconstruction on the basis of the raw data acquired according to the invention is shown in FIG. 8. Changes with regard to a conventional PROPELLER reconstruction are thereby respectively marked with a frame drawn with a dash-dot line.

As in the prior art, the various slices are reconstructed independently of one another. The reconstruction of a single slice is thus shown. In contrast to the prior art, a portion of the propeller blades of the slice is acquire twice in different echo groups, while only a single segment data set is present per alignment for the propeller blades acquired in CPMG mode. The goal of the modified reconstruction is to combine the doubly acquired propeller blades with the same alignment after a number of method steps so that—as in the prior art—precisely one segment data set exists per direction, and the remaining method steps can be implemented conventionally.

A PROPELLER reconstruction normally starts with a few method steps that respectively operate only on the data of a segment. The modified reconstruction thereby differentiates whether the respective blade was acquired twice in two echo groups or once. In the first case (also designated as a NON-CPMG mode in the following), the segment data set acquired in the first echo signal group $E_{1a}$ or, respectively, $E_{2a}$ enters the reconstruction pipeline via the input designated with $E_{1a}/E_{2a}$ (in the workflow diagram in FIG. 8), and the respective associated segment data set acquired in the second echo signal group $E_{1b}$ or $E_{2b}$. Given a single acquisition in the echo signal group $E_3$ in CPMG mode, the input designated with $E_3$ is to be selected.

Insofar as a parallel reconstruction technique was used with multiple reception coils, the respective lines of the segment that are not acquired are substituted with the assistance of the coil calibration data (for example the coil sensitivities of the individual coils) in method steps I.1/2a, II.1/2b, I.3. In the simplest case, this method step does not differ from the corresponding method step in the conventional PROPELLER reconstruction. Optionally, in the NON-CPMG case the duplicate presence of the data set can advantageously be utilized, for example to achieve a better signal-to-noise ratio, reduction of remaining artifacts or sparing of computing capacities.

Propeller blades of a specific slice with the same rotation angle that were acquired twice in two readout windows can subsequently (after the slowly varying phase in image space was computationally removed in steps II.1/2a or, respectively, II.1/2b) be combined as complex values in Step III.1/2. The details of the method steps II.1/2a, II.1/2b and III.1/2 can be taken from the method explained above with the assistance of FIG. 6. The single difference here is that the operations take place at single segment data sets, and not at the complete, doubly acquired k-space data set of a slice. A segment data set acquired once in CPMG mode is likewise phase-corrected in Step II.3.

After the complex-value combination of the propeller blades that are acquired twice in the NON-CPMG mode, one completed, phase-corrected propeller blade segment data set $Bl_x$, $Bl_y$ is presented per alignment (rotation angle of the propeller blade). The remaining method steps can thus be implemented as in the conventional PROPELLER reconstruction. The remaining method steps comprise an optional movement detection (Steps IV.1/2, IV.3), a density compensation (for example in Steps V.1/2, V.3), and finally a combination of the propeller blades with varying alignment in k-space, a final two-dimensional Fourier transformation into image space, and possibly additional optional steps such as filter operations (all steps jointly represented by the block Step VI), for example. The combination of the propeller blades with different alignment is normally implemented as what is known as a "gridding" operation. This step can also optionally be implemented with subsequent accumulation as described in DE 10 2005 046 732, for example. Details of the conventional PROPELLER reconstruction are found in the previously cited journal article by James Pipe.

A density compensation is reasonable since the central regions of k-space are acquired repeatedly via different propeller blades, while the peripheral region is normally acquired only once. The density compensation before the combination of the propeller blades is implemented in FIG. 6 with different alignment than Step V.1/2 or, respectively, V.3. In the density compensation, the higher signal strength of the propeller blades acquired in the featured CPMG mode can also optionally be taken into account in addition to the different densities of acquisition of the k-space data. But, this is not absolutely necessary. However, artifacts as a result of signal differences are also avoided in the simple embodiment since k-space points that are close to the center (which k-space points define the contrast and image impression and are therefore artifact-sensitive) are acquired repeatedly by different propeller blades, and thus average out the signal differences.

Figure 9:
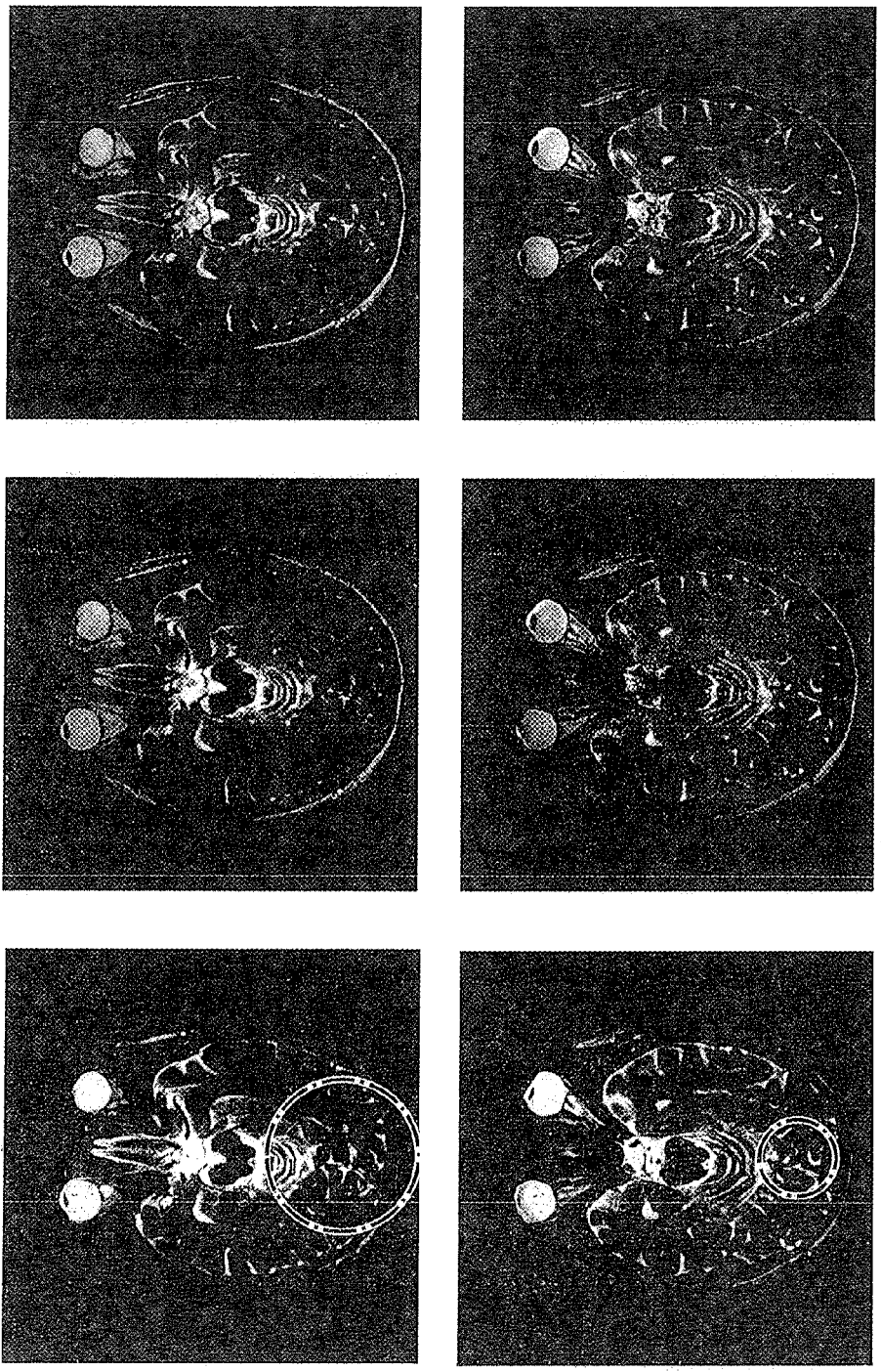
FIG. 9 shows an example of slice images for comparison of the measurements with a conventional one-slice TSE pulse sequence, and two different multislice TSE pulse sequences according to the invention.
Figure 10:
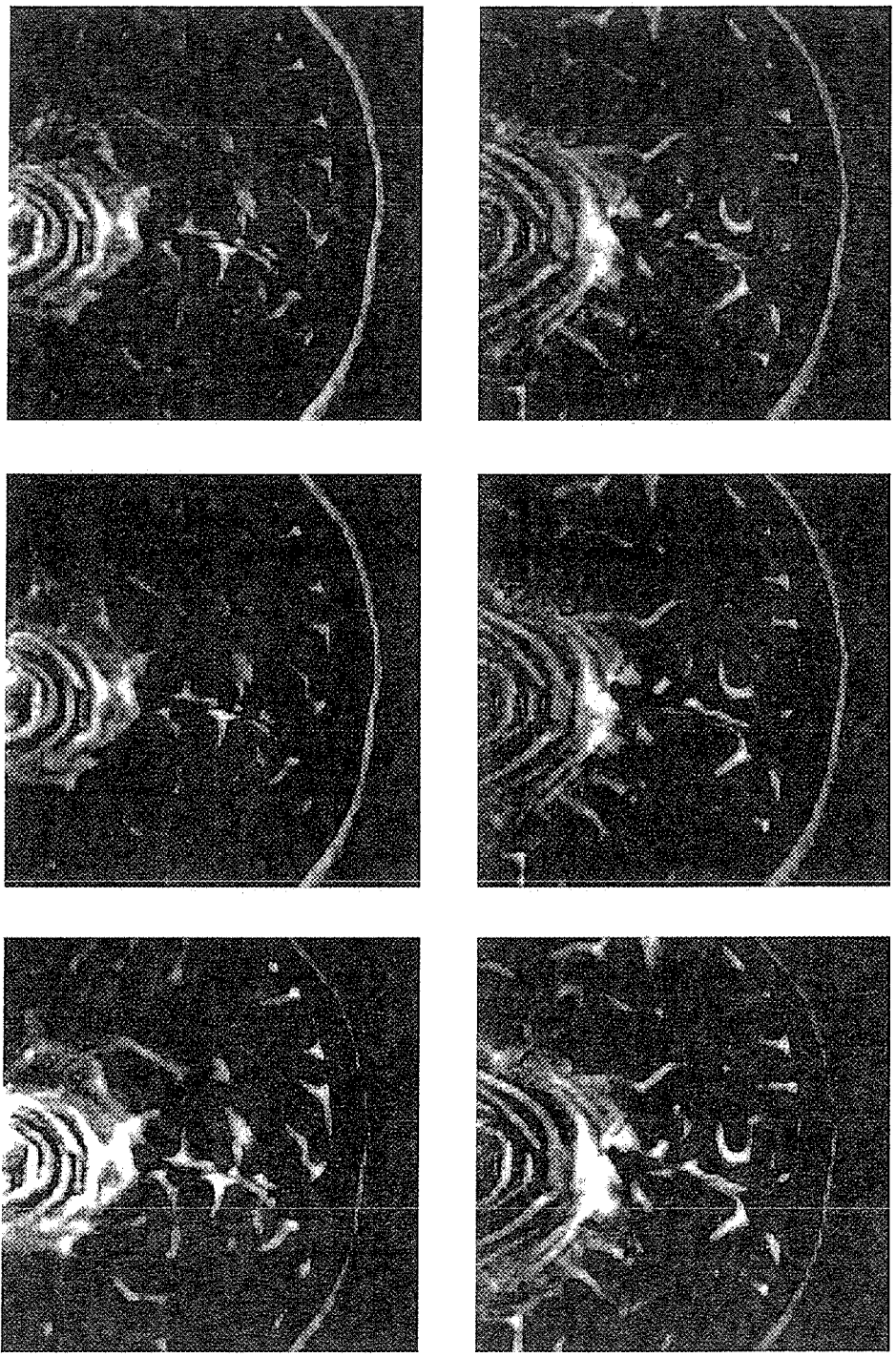
FIG. 10 shows enlargements of the exemplary slice images of FIG. 9.

FIGS. 9 through 11 show head images acquired with a 3 Tesla magnetic resonance tomograph. The images in the left column are respectively acquired with a PROPELLER/BLADE turbo spin echo sequence that is separately refocused (i.e. with m=1) and known from the prior art. The images in the second and third column were acquired with a PROPELLER/BLADE turbo spin echo sequence according to the invention that respectively simultaneously refocuses two adjacent slices (i.e. with m=2). Images of one line respectively show the same slice $S_1$, $S_2$ (as an example for 28 acquired slices in total). The two shown slices were thereby simultaneously refocused insofar as it was acquired with the sequence according to the invention (thus in columns two and three). The difference between the images of the second and third column is that, given acquisition of the images of the third column according to the variant explained above in connection with FIG. 7, the relative time position of the excitation pulses of the two slices was changed after the acquisition of the propeller blades with odd index in order to avoid contrast and SNR differences of different slices.

FIGS. 10 and 11 respectively show an enlarged section of the images shown in FIG. 9. The section enlarged in FIG. 10 is marked by the respective circle with the dash-dot border in the left upper image of FIG. 9, and the section enlarged in FIG. 11 is marked by the respective circle with the dash-dot border in the left lower image of FIG. 9.

In order to enable an optimally realistic comparison, the parameters of the compared sequences are largely selected to be identical, with the following exceptions:

The readout bandwidth BW of the conventional (m=1) sequence was reduced (BW=130 Hz per pixel, relative to 407 Hz per pixel in the sequences according to the invention) in order to achieve the same echo spacing given respective complete utilization of the available acquisition time.

The repetition time TR of the conventional sequence was doubled to TR=6000 ms (relative to TR=3000 ms of the sequences according to the invention) in order to comply with the regulated SAR limits. The acquisition time per image of the conventional sequence, at 18×6000 ms=106 seconds, is accordingly twice as long as in the sequences according to the invention.

The common sequence parameters were as follows:

A 256-element matrix was used, which leads to an in-plane resolution (pixel spacing) of 0.85×0.85 mm$^2$ given a quadratic field of view with 220 mm edge length.

18 propeller blades were measured per slice.

The slice thickness was Δ4 mm, and the slice gap was 30% of the slice thickness, i.e. 1.2 mm, which leads to a middle distance of d=5.2 mm.

28 slices were measured in total to cover the head, wherein 14 slices were respectively excited per respective repetition time TR.

The nominal flip angle of the refocusing pulses was 140°.

As the images show, no differences in the imaged anatomy are apparent between the images of a line. This is particularly well apparent in the imaging 10 given a comparison of the details of the cerebellum structure. The separation of the slices is thus perfect. This is therefore in particular also a very good result since measurement was made with clinically relevant slice thickness and slice interval. The tissue contrast is thereby comparable.

The measurement time could be approximately halved with the sequence according to the invention with two simultaneously excited and refocused slices. The measurement time was thereby primarily SAR-limited for both protocols. Apart from an approximately doubled SAR exposure, the shorter repetition time TR would also not be realizable with the conventional sequence given the same total slice count, since the simultaneously refocused conventional sequence is also more time-efficient by approximately a factor of m at a given echo spacing. In contrast to this, with the sequence according to the invention it would be possible to also measure more than 14 slices with the cited parameters and a repetition time TR of 3000 ms.

A comparison of the images in the first line of the second column with the image of the second line of the second column shows that the signal-to-noise ratio of the image of the first line that is acquired in the featured CPMG mode is markedly better. The corresponding images show no perceptible SNR difference in the third column. This supports the situation that slice variations in the signal-to-noise ratio can be avoided without further measures (if this is desired) via the method according to the invention given a variation of the time position of the excitation pulses.

It should be noted that the term "complete raw data set" in connection with the present invention disclosure designates a data set with which an image can be reconstructed in the prior art. This thus includes data sets in which individual raw data lines (which are necessary for image reconstruction by means of fast Fourier transformation, for example) were not acquired and, for example, must still be substituted with parallel reconstruction techniques.

Furthermore, a complete raw data set can be acquired with a single echo train (as shown in FIG. 2) or via multiple repetition of the sequence from FIG. 2, wherein different k-space lines are generally acquired in different repetitions. The first procedure corresponds to what are known as single shot variants HASTE or RARE in the conventional turbo spin echo technique, the second to what are known as multi-shot variants, with corresponding advantages and disadvantages.

If the first time interval $T_\alpha$ is greater than the duration $T_{ACQ}$ of a readout window, in a further modification an additional gradient pulse can also respectively be switched between two readout windows for further separation of the echo signals. The moment of this additional gradient would then only be taken into account in the calculation of the gradients $GR_{1,0}$, $GR_{0,2}$ switched in the readout direction between the excitation pulses, so that the moment in the readout direction is respectively equal to zero again at the echo point in time.

The sequence according to the invention is compatible with the most important non-Cartesian k-space trajectories, for example PROPELLER sequences (see the exemplary embodiment explained in connection with FIGS. 7 and 8), spiral sequences, sequences with concentric rings or radial sequences.

It is also possible to form multiple echoes per echo group via a series of readout gradients with alternating amplitude, as in an EPI sequence, and to code these as in a GRASE method, for example (gradient and spin echo method, as is described in "GRASE (Gradient- and Spin-Echo) Imaging: A Novel Fast MRI technique"; Magnetic Resonance in Medicine, 20, 1991, P. 344-349) to reduce the acquisition time. Alternatively, the time interval of the readout gradients of an echo group can thereby be selected such that a desired phase shift is achieved between water component and fat component of the read-out signal. With the use of the known Dixon reconstruction, images that respectively show only the fat component or, respectively, only the water component of the examined tissue can then be reconstructed from the different images of an echo group that are obtained in such a manner.

The pulse sequences according to the invention are then also in the position to maintain an echo train that is sufficiently long for the fast T2-weighted imaging when the flip angle of the refocusing pulses is significantly reduced relative to 180°. This is advantageous in particular given a use in high field systems with a basic magnetic field of 3 Tesla or more in order to arrive at a sufficient reduction of the SAR exposure given a moderate slice count m (and therefore a moderate extension of the echo spacing). For reasons of SAR reduction, the sequence according to the invention is therefore even often preferably used with reduced flip angles of the refocusing pulses. A refocusing flip angle of 90° led to no impairment of the image quality in a test. This is an advantage relative to possible alternative approaches, for example the phase modulation of RF pulse applied by Patrick Le Roux and James Pipe in connection with the separately refocused diffusion-weighted imaging; see for example "Multishot diffusion-weighted FSE using PROPELLER MRI" by James G. Pipe, Victoria G. Farthing, Kirsten P. Forbes, appearing in the journal Magnetic Resonance in Medicine 47:42-52 (2002)), with which it could be attempted to stabilize the echo train.

Although all refocusing pulses in Figures are depicted in the same manner, different refocusing pulses can in particular also have different flip angles.

The sequence is also compatible with what are known as variable rate (VR) or, respectively, variable rate selective excitation (VERSE) pulses, with which a reduction of the radiated RF energy is achieved in that the peak amplitude of the radio-frequency pulse is reduced in comparison to a corresponding SINC pulse.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to operate a magnetic resonance tomography system having a magnetic resonance data acquisition scanner that has a radio-frequency (RF) radiator and a gradient coil arrangement comprising:

operating the RF radiator to excite nuclear spins in a plurality of slices in an examination subject in said magnetic resonance data acquisition scanner at a first time interval by radiating a series of spatially selective RF slice excitation pulses, with each RF slice excitation pulse in said series exciting nuclear spins in a respective slice in said plurality of slices;

operating the RF radiator to emit an RF refocusing pulse in said magnetic resonance data acquisition scanner at a second time interval after a first RF excitation pulse or after a last RF excitation pulse in said series of spatially selective RF slice excitation pulses, and emitting at least one additional RF refocusing pulse at a third time interval after a preceding RF refocusing pulse, with said third interval to being twice as long as said second time interval, and with each of said RF refocusing pulses having a width so as to generate a plurality of chronologically successive separate echo signals for each RF refocusing pulse, with each RF refocusing pulse being simultaneously effective in multiple excited slices among said plurality of slices;

operating the gradient coil arrangement to read out said echo signals for each refocusing pulse under a readout gradient in a corresponding number of readout windows; and providing the echo signals that have been read out to a processor and in said processor, converting said echo signals into magnetic resonance data and making said magnetic resonance data available from said processor in electronic form, as a data file.

2. A method as claimed in claim 1 comprising operating said gradient coil arrangement to activate said gradient pulse series between two successive RF slice excitation pulses that have a 0th moment equal to an accumulated 0th moment of said gradient pulse series.

3. A method as claimed in claim 2 comprising operating said gradient coil arrangement to activate said gradient pulse series with the 0th moment of all gradient pulses activated in the slice selection direction between isodelay points of two successive RF excitation pulses being zero.

4. A method as claimed in claim 2 comprising operating said gradient coil arrangement to activate said gradient pulse series with a 0th moment accumulated as a result of an activated gradient pulse in said readout direction between said last RF excitation pulse and a first RF refocusing pulse in said series of RF refocusing pulses being equal to the 0th moment accumulated in the readout direction between said first of said RF refocusing pulses and a first of said echo signals.

5. A method as claimed in claim 1 comprising operating said RF radiator with a time duration of each RF slice excitation pulse being shorter than a time duration of any RF refocusing pulse.

6. A method as claimed in claim 5 comprising operating said gradient coil arrangement to activate said gradient pulse series to scan respective k-spaces of the respective slices in a single echo train either once or twice.

7. A method as claimed in claim 5 comprising operating said magnetic resonance data acquisition scanner with a pulse sequence comprised of multiple sequence modules, each having an echo train, and acquiring raw data of at least two segments of k-space for each slice with each echo train.

8. A method as claimed in claim 7 comprising operating said magnetic resonance data acquisition scanner to segment the respective k-spaces according to a PROPELLER trajectory.

9. A method as claimed in claim 7 comprising operating said magnetic resonance data acquisition scanner to acquire said magnetic resonance data from different segments of a respective slice in different sequence modules, with a timing of the respective RF slice excitation pulse for the respective slice being varied from pulse sequence-to-pulse sequence.

10. A method as claimed in claim 5 comprising:
operating said RF radiator to excite said plurality of slices in a magnetic resonance pulse sequence module comprising a plurality of readout windows and operating said gradient coil arrangement to acquire the data from the respective slices in respectively different ones of said readout windows individually associated with respective RF refocusing pulses;
in said processor, calculating separate magnitude images from the magnetic resonance data acquired from the plurality of readout windows; and
in said processor, combining said magnitude images associated with a same slice into a single slice image of said same slice, and making said single slice image available from said processor in electronic form as am image data file.

11. A method as claimed in claim 10 comprising combining said magnitude images in said processor using a sum-of-squares technique.

12. A method as claimed in claim 5 comprising:
operating said RF radiator to excite said plurality of slices in a magnetic resonance pulse sequence module comprising a plurality of readout windows and operating the gradient coil arrangement to acquire the data from the respective slices in respectively different ones of said readout windows individually associated with respective RF refocusing pulses; and
in said processor, calculating image data from said magnetic resonance data and combining image data of a respective slice that were acquired with a single echo train in different ones of said readout windows in a complex-value combination of said image data.

13. A method as claimed in claim 12 comprising combining said image data after computationally removing a phase associated with the image data.

14. A control device to operate a magnetic resonance tomography system comprising:
a computerized control unit comprising an interface configured to place said control unit in communication with a magnetic resonance data acquisition scanner to provide control signals to said magnetic resonance data acquisition scanner to excite nuclear spins in a plurality of slices in an examination subject in said magnetic resonance data acquisition scanner at a first time interval by radiating a series of spatially selective RF slice excitation pulses, with each RF slice excitation pulse in said series exciting nuclear spins in a respective slice in said plurality of slices;
said control unit being configured to cause said data acquisition unit to emit an RF refocusing pulse in said data acquisition scanner at a second time interval after a first RF excitation pulse or after a last RF excitation pulse in said series of spatially selective RF excitation pulses, and to emit at least one additional RF refocusing pulse at a third time interval after a preceding RF refocusing pulse; and
said control unit being configured to set said third time interval to be twice as long as said second time interval, and to set a width of each of said RF refocusing pulses so as to generate a plurality of chronologically successive separate echo signals for each RF refocusing pulse, with each RF refocusing pulse being simultaneously effective in multiple excited slices among said plurality of slices.

15. A magnetic resonance tomography apparatus comprising:
a magnetic resonance data acquisition scanner;
a control computer configured to operate said data acquisition scanner to excite nuclear spins in a plurality of slices in an examination subject in said magnetic resonance data acquisition scanner at a first time interval by radiating a series of spatially selective RF slice excitation pulses, with each RF slice excitation pulse in said series exciting nuclear spins in a respective slice in said plurality of slices;
said control computer being configured to operate said data acquisition scanner to emit an RF refocusing pulse in said data acquisition unit at a second time interval after a first RF excitation pulse or after a last RF excitation pulse in said series of spatially selective RF excitation pulses, and to emit at least one additional RF refocusing pulse at a third time interval after a preceding RF refocusing pulse; and
said control computer being configured to set said third time interval to be twice as long as said second time interval, and to set a width of each of said RF refocusing pulses so as to generate a plurality of chronologically successive separate echo signals for each RF refocusing pulse, with each RF refocusing pulse being simultaneously effective in multiple excited slices among said plurality of slices.

16. A non-transitory, computer-readable data storage medium encoded with programming instructions, said storage medium being loaded into a computerized control and evaluation computer system of a magnetic resonance tomography system that also comprises a magnetic resonance data acquisition scanner, said programming instructions causing said control and evaluation computer system to:

operate said data acquisition scanner to excite nuclear spins in a plurality of slices in an examination subject in said magnetic resonance data acquisition scanner at a first time interval by radiating a series of spatially selective RF slice excitation pulses, with each RF slice excitation pulse in said series exciting nuclear spins in a respective slice in said plurality of slices;

operate said data acquisition scanner to emit an RF refocusing pulse in said data acquisition unit at a second time interval after a first RF excitation pulse or after a last RF excitation pulse in said series of spatially selective RF excitation pulses, and to emit at least one additional RF refocusing pulse at a third time interval after a preceding RF refocusing pulse; and set said third time interval to be twice as long as said second time interval, and set a width of each of said RF refocusing pulses so as to generate a plurality of chronologically successive separate echo signals for each RF refocusing pulse, with each RF refocusing pulse being simultaneously effective in multiple excited slices among said plurality of slices.

* * * * *